US012705677B2

(12) United States Patent
Cope et al.

(10) Patent No.: US 12,705,677 B2
(45) **Date of Patent: *Aug. 11, 2026**

(54) SYSTEMS AND METHODS FOR DETECTING BUILDING EVENTS AND TRENDS

(71) Applicant: State Farm Mutual Automobile Insurance Company, Bloomington, IL (US)

(72) Inventors: Craig Benjamin Cope, Bloomington, IL (US); Emily Kate Schneider, Bloomington, IL (US); Kara Lynn Heuer, Normal, IL (US); Burton J. Floyd, Mackinaw, IL (US); Kevin Joseph Alcozar, Bloomington, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/665,139

(22) Filed: May 15, 2024

(65) Prior Publication Data

US 2024/0303757 A1 Sep. 12, 2024

Related U.S. Application Data

(63) Continuation of application No. 16/677,247, filed on Nov. 7, 2019, now Pat. No. 12,008,667.

(Continued)

(51) Int. Cl.

*G06Q 50/163* (2024.01)
*G06N 5/04* (2023.01)

(Continued)

(52) U.S. Cl.

CPC ............ *G06Q 50/163* (2013.01); *G06N 5/04* (2013.01); *G06N 20/00* (2019.01); *G06Q 10/20* (2013.01);

(Continued)

(58) Field of Classification Search

CPC ........ G16Y 10/80; G16Y 20/10; G16Y 20/40; H04L 12/1895; H04L 67/12; G06Q 50/163; G08B 19/00

See application file for complete search history.

(56) References Cited

U.S. PATENT DOCUMENTS 6,934,692 B1 8/2005 Duncan
7,356,516 B2 4/2008 Richey et al.

(Continued)

FOREIGN PATENT DOCUMENTS

AU 2015100551 A4 5/2015
WO 2018052595 A1 3/2018

OTHER PUBLICATIONS

Weimin Huang, Tuan Kiang Chiew, Haizhou Li, Tian Shiang Kok and Jit Biswas, "Scream detection for home applications," 2010 5th IEEE Conference on Industrial Electronics and Applications, Taichung, Taiwan, 2010, pp. 2115-2120, doi: 10.1109/ICIEA.2010.5515397 (Year: 2010).*

(Continued)

*Primary Examiner* — Jason D Recek
(74) *Attorney, Agent, or Firm* — Armstrong Teasdale LLP

(57) ABSTRACT

A building analysis ("BA") system for detecting events of a building includes a plurality of sensors positioned within a building, at least one memory device and a building analysis ("BA") computing device communicatively coupled to the plurality of sensors, the BA computing device comprising one or more processors in communication with the at least one memory device, wherein the one or more processors are programmed to build an infrastructure profile for the infrastructure, the infrastructure profile including i) one or more reference parameters, ii) detected historic conditions of the one or more fixtures using historical sensor data received over a period of time, and iii) detected historic conditions of (Continued)

the at least one person using historical sensor data received over a period of time.

19 Claims, 11 Drawing Sheets

Related U.S. Application Data

(60) Provisional application No. 62/835,269, filed on Apr. 17, 2019, provisional application No. 62/820,650, filed on Mar. 19, 2019, provisional application No. 62/802,435, filed on Feb. 7, 2019.

(51) Int. Cl.
*G06N 20/00* (2019.01)
*G06Q 10/20* (2023.01)
*G06Q 20/10* (2012.01)
*G06Q 30/018* (2023.01)
*G06Q 30/0283* (2023.01)
*G06Q 40/02* (2023.01)
*G06Q 40/08* (2012.01)
*G06Q 40/12* (2023.01)
*G06Q 50/26* (2012.01)
*G08B 19/00* (2006.01)
*G16H 50/30* (2018.01)
*G16H 70/60* (2018.01)
*G16Y 10/80* (2020.01)
*G16Y 20/10* (2020.01)
*G16Y 20/40* (2020.01)
*H04L 12/18* (2006.01)
*H04L 67/12* (2022.01)

(52) U.S. Cl.
CPC ......... *G06Q 20/108* (2013.01); *G06Q 30/018* (2013.01); *G06Q 30/0283* (2013.01); *G06Q 40/02* (2013.01); *G06Q 40/08* (2013.01); *G06Q 40/125* (2013.12); *G06Q 50/265* (2013.01); *G08B 19/00* (2013.01); *G16H 50/30* (2018.01); *G16H 70/60* (2018.01); *G16Y 10/80* (2020.01); *G16Y 20/10* (2020.01); *G16Y 20/40* (2020.01); *H04L 12/1895* (2013.01); *H04L 67/12* (2013.01)

(56) References Cited

U.S. PATENT DOCUMENTS 7,395,219 B2 7/2008 Strech
7,657,441 B2 2/2010 Richey et al.
8,172,154 B1 5/2012 Figley et al.
8,433,344 B1 4/2013 Virga
8,600,556 B2 12/2013 Nesler et al.
8,712,805 B1 4/2014 Ferries et al.
9,980,116 B2 5/2018 Slevin et al.
9,986,313 B2 5/2018 Schwarzkopf et al.
10,013,861 B2 7/2018 Fadell et al.
10,055,793 B1 8/2018 Call et al.
10,062,118 B1 8/2018 Bernstein et al.
10,137,984 B1 11/2018 Flick
10,217,068 B1 2/2019 Davis et al.
10,229,394 B1 3/2019 Davis et al.
10,352,504 B2 7/2019 Dietzen et al.
10,387,966 B1 8/2019 Shah et al.
10,497,250 B1 12/2019 Hayward et al.
10,623,509 B2 4/2020 Delinselle et al.
10,672,081 B1 6/2020 Lyons et al.
10,699,346 B1 6/2020 Corder et al.
10,861,115 B1 12/2020 Stricker et al.
10,943,463 B1 3/2021 Clark
11,003,334 B1 5/2021 Conway et al.
11,017,781 B2 5/2021 Cilingir et al.
11,037,255 B1 6/2021 Ganev et al.
11,043,090 B1 6/2021 Ulen
11,055,797 B1 7/2021 Carone
11,087,347 B1 8/2021 De Guia et al.
11,087,420 B1 8/2021 Trundle
11,210,741 B1 12/2021 Allen et al.
11,328,363 B1 5/2022 Brannan et al.
11,501,100 B1 11/2022 Geng et al.
11,656,097 B2 5/2023 Vega et al.
11,748,817 B2 9/2023 Szott
2001/0038336 A1 11/2001 Acevedo
2004/0153382 A1 8/2004 Boccuzzi et al.
2007/0194922 A1 8/2007 Nathan et al.
2008/0059351 A1 3/2008 Richey et al.
2008/0255862 A1 10/2008 Bailey et al.
2009/0024420 A1 1/2009 Winkler
2010/0131416 A1 5/2010 Means
2011/0270773 A1 11/2011 Siekman et al.
2011/0295624 A1 12/2011 Chapin et al.
2012/0022700 A1 1/2012 Drees et al.
2012/0046973 A1 2/2012 Eshleman et al.
2012/0072239 A1 3/2012 Gibbard et al.
2012/0232935 A1 9/2012 Voccola
2013/0073321 A1 3/2013 Hofmann et al.
2013/0166325 A1 6/2013 Ganapathy et al.
2013/0169430 A1 7/2013 Shook
2014/0129160 A1 5/2014 Tran
2014/0136242 A1 5/2014 Weekes et al.
2014/0229205 A1 8/2014 Gibson
2014/0257871 A1 9/2014 Christensen et al.
2014/0278576 A1 9/2014 Mariyal et al.
2014/0320295 A1 10/2014 Kates
2015/0032480 A1 1/2015 Blackhurst et al.
2015/0061859 A1 3/2015 Matsuoka et al.
2016/0026729 A1 1/2016 Gil et al.
2016/0048934 A1 2/2016 Gross
2016/0055594 A1 2/2016 Emison et al.
2016/0163186 A1* 6/2016 Davidson ............... G06Q 50/06 340/506
2016/0210569 A1 7/2016 Enck
2016/0275633 A1 9/2016 Gitt et al.
2016/0321587 A1 11/2016 Gitt et al.
2017/0180147 A1 6/2017 Brandman et al.
2017/0292725 A1 10/2017 Conley et al.
2017/0365186 A1* 12/2017 Ingram ................ G06Q 10/109
2018/0033087 A1 2/2018 Delinselle et al.
2018/0106897 A1 4/2018 Shouldice et al.
2018/0121571 A1 5/2018 Tiwari et al.
2018/0169451 A1 6/2018 Moffa
2018/0254041 A1 9/2018 Harper
2019/0096147 A1 3/2019 Park et al.
2019/0127985 A1 5/2019 Dundorf et al.
2019/0128771 A1 5/2019 Santarone et al.
2019/0129780 A1 5/2019 DelSordo et al.
2019/0171171 A1 6/2019 Verteletskyi et al.
2019/0251520 A1 8/2019 Bentley, III et al.
2019/0294136 A1 9/2019 Iacobone et al.
2020/0054238 A1 2/2020 Gopinathan et al.
2020/0090289 A1* 3/2020 Elbsat .................... G06Q 10/04
2021/0011448 A1 1/2021 Coleman et al.
2021/0018335 A1 1/2021 Hood
2021/0019847 A1 1/2021 Sneed
2021/0150651 A1 5/2021 Shoup
2021/0166322 A1 6/2021 Allen et al.
2021/0182986 A1 6/2021 Butler et al.
2021/0279791 A1 9/2021 Jacoby
2021/0350471 A1 11/2021 Hakimi-Boushehri et al.
2022/0005121 A1 1/2022 Hayward
2022/0343443 A1 10/2022 Graham et al.
2022/0391794 A1 12/2022 Singh et al.
2023/0035517 A1 2/2023 Bentley, III et al.

OTHER PUBLICATIONS

Karlsruhe Institute of Technology, "Sensor detects cable fire before it starts burning", Web Article, Phys. org, Nov. 26, 2015, 2 pages.

(56) References Cited

OTHER PUBLICATIONS

Takei et al., "Odor Sensor System for Early Fire Detection and Its Application to Utility Mobile Robot", Sensors and materials 17.7 (2005): 413-421.
Takei et al., "Odor Sensor System for Early Fire Detection and Its Application to Utility Mobile Robot", 1 page.
Liu et al., "Design and Implementation of Smart-Home Monitoring System with the Internet of Things Technology," p. 5, Jan. 2016. Retrieved from: https://www.researchgate.net/publication/300330870_Design_and_Implementation_of_Smart-Home_Monitoring_System_with_the_Internet_of_Things_Technology.
Michalis et al., "Quality Evaluation of Residential Houses: The Development of a Real-Time Quality Assessment Tool," p. 11-12, Jan. 2013. Retrieved from: https://www.researchgate.net/publication/233841366_Quality_Evaluation_of_Residential_Houses_The_Development_of_a_Real-Time_Quality_Assessment_Tool.
Moore et al., "An intelligent maintenance system for continuous cost-based prioritisation of maintenance activities," Aug. 2006. Retrieved from: https://www.researchgate.net/publication/222428855_An_intelligent_maintenance_system_for_continuous_cost-based_prioritisation_of_maintenance_activities.
Spoor et al., "How can data generated by smart home devices help identify consumer needs?," p. 7, Jul. 2016. Retrieved from: https://essay.utwente.nl/69990/1/Spoor_BA_BMS.pdf.

* cited by examiner

SYSTEMS AND METHODS FOR DETECTING BUILDING EVENTS AND TRENDS

CROSS-REFERENCE TO RELATED APPLICATIONS

This application is a continuation of and claims the benefit of priority to U.S. patent application Ser. No. 16/677,247, filed Nov. 7, 2019, entitled "SYSTEMS AND METHODS FOR DETECTING BUILDING EVENTS AND TRENDS," which further claims priority to U.S. Provisional Patent Application No. 62/802,435, filed Feb. 7, 2019, entitled "SYSTEMS AND METHODS FOR DETECTING BUILDING EVENTS AND TRENDS," to U.S. Provisional Patent Application No. 62/820,650, filed Mar. 19, 2019, entitled "SYSTEMS AND METHODS FOR DETECTING BUILDING EVENTS AND TRENDS," and to U.S. Provisional Patent Application No. 62/835,269, filed Apr. 17, 2019, entitled "SYSTEMS AND METHODS FOR DETECTING BUILDING EVENTS AND TRENDS," the entire contents and disclosure of which are hereby incorporated by reference herein in their entirety.

FIELD OF THE DISCLOSURE

The present disclosure relates to maintaining a building and, more particularly, to systems and methods for monitoring the health of a building and its occupants to detect events and trends.

BACKGROUND

Failure of a building's structural component, building system, or home device, such as an electronic appliance may not immediately be evident until evidence of damage, deterioration, or failure presents itself more apparently to the homeowner. In many cases, building system failures may lead to additional damage to the building. For example, one eventual visual indicator for an undetected roof leak may be a resulting dark spot or stain of dampness and/or mold growth on the ceiling of an interior roof where the leak dripped over the course of many rains.

This additional or ancillary damage created by the undetected compromise may cause building owners to have to spend significantly more to repair the building, as they pay to fix not only the underlying system failure (e.g., the leaky roof) but also the damage caused by not promptly detecting the failure (e.g., the mold growth in an attic and the staining on the interior ceiling).

In many cases, a homeowner may be presented with a visual, auditory, or other sensory indicator as to a symptom of a building failure or compromise, but have difficulty determining the underlying source of the system failure. In other cases, a homeowner may be unaware of hazardous building compromises, such as gas leaks, because the homeowner cannot detect any sensory indicators. For example, a homeowner may be unable to detect a gas leak because there is no accompanying gas odor or simply because the homeowner cannot smell gas. Accordingly, early detection of faults or compromises in various building systems may be desirable.

BRIEF SUMMARY

The present embodiments may relate to systems and methods for monitoring a building to detect building events and trends. The system may include a plurality of sensors positioned within a building. The plurality of sensors may be configured to detect an infrastructure associated with the building, such as a (i) fixture included within or part of the building, and/or (ii) person(s) located within the building. Fixtures may include items within a building (e.g., electronic devices, appliances, water heater, air conditioner, furnace), building materials (e.g., materials associated with a building's pipes, roof, walls (exterior and interior), flooring), and zones of a building's premises (e.g., rooms, garage, hallway, attic, basement, patio, backyard). The system may also include a memory device including an infrastructure profile for each infrastructure being monitored by the system. The system may further include an optimal profile for each infrastructure being monitored by the system. The optimal profile may include infrastructure characteristics representing an optimal condition for the infrastructure being monitored.

The system may further include a building analysis (BA) server. The BA server may be communicatively coupled to the plurality of sensors. The BA server may include one or more processors in communication with the memory device. The BA server may be programmed to: (i) receive, from the plurality of sensors, sensor data related to an infrastructure, the infrastructure being at least one of a fixture and/or at least one person located within the building; (ii) analyze the sensor data to identify the infrastructure; (iii) apply a prediction model to the sensor data to detect an event associated with the infrastructure, (iv) generate an alert message that includes a recommended action for a building owner (e.g., homeowner); and/or (v) transmit the alert message to a user computing device associated with the building owner. The BA server may also be programmed to direct or control the taking of the recommended action to mitigate or prevent damage to the building or mitigate or prevent injury to the at least one person.

In one aspect, a building analysis ("BA") system for detecting events of a building may be provided. The BA system may include a plurality of sensors positioned within a building. The plurality of sensors may be configured to detect a condition associated with an infrastructure of the building. The infrastructure may be at least one of (i) a fixture associated with the building, and (ii) at least one person located within the building. The BA system may also include a memory device including an optimal profile of the infrastructure. The optimal profile may include characteristics representative of an optimal condition for the infrastructure. The BA system may also include a building analysis ("BA") server communicatively coupled to the plurality of sensors. The BA server may include one or more processors in communication with the memory device.

The one or more processors may be programmed to: (i) receive, from the plurality of sensors, sensor data related to the infrastructure, (ii) compare the received sensor data to the optimal profile to detect an event associated with the infrastructure, (iii) generate, based upon the comparison, an alert message that includes the detected event and a recommended action for an owner of the building, wherein the recommended action is at least one of a preventative action or a corrective action, and/or (iv) transmit the alert message to a user computing device associated with the owner of the building. The one or more processors may also be programmed to direct or carryout the recommended action. The BA computer system may include additional, less, or alternate functionality, including those discussed elsewhere herein.

In another aspect, a computer-implemented method for detecting events of a building may be provided. The method may be implemented using a building analysis ("BA") system. The BA system may include (a) a plurality of sensors positioned within a building. The plurality of sensors may be configured to detect a condition associated with an infrastructure of the building. The infrastructure may be at least one of (i) a fixture associated with the building, and (ii) at least one person located within the building. The BA system may also include (b) a memory device including an optimal profile of the infrastructure. The optimal profile may include characteristics representative of an optimal condition for the infrastructure. The BA system may also include (c) a building analysis ("BA") server communicatively coupled to the plurality of sensors. The BA server may include one or more processors in communication with the memory device.

The computer-implemented method may include: (i) receiving, from the plurality of sensors, sensor data related to the infrastructure, (ii) comparing the received sensor data to the optimal profile to detect an event associated with the infrastructure, (iii) generating, based upon the comparison, an alert message that includes the detected event and a recommended action for an owner of the building, wherein the recommended action is at least one of a preventative action or a corrective action, and/or (iv) transmitting the alert message to a user computing device associated with the owner of the building. The BA computer-implemented method may include additional, less, or alternate functionality, including those discussed elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

Figure 1:
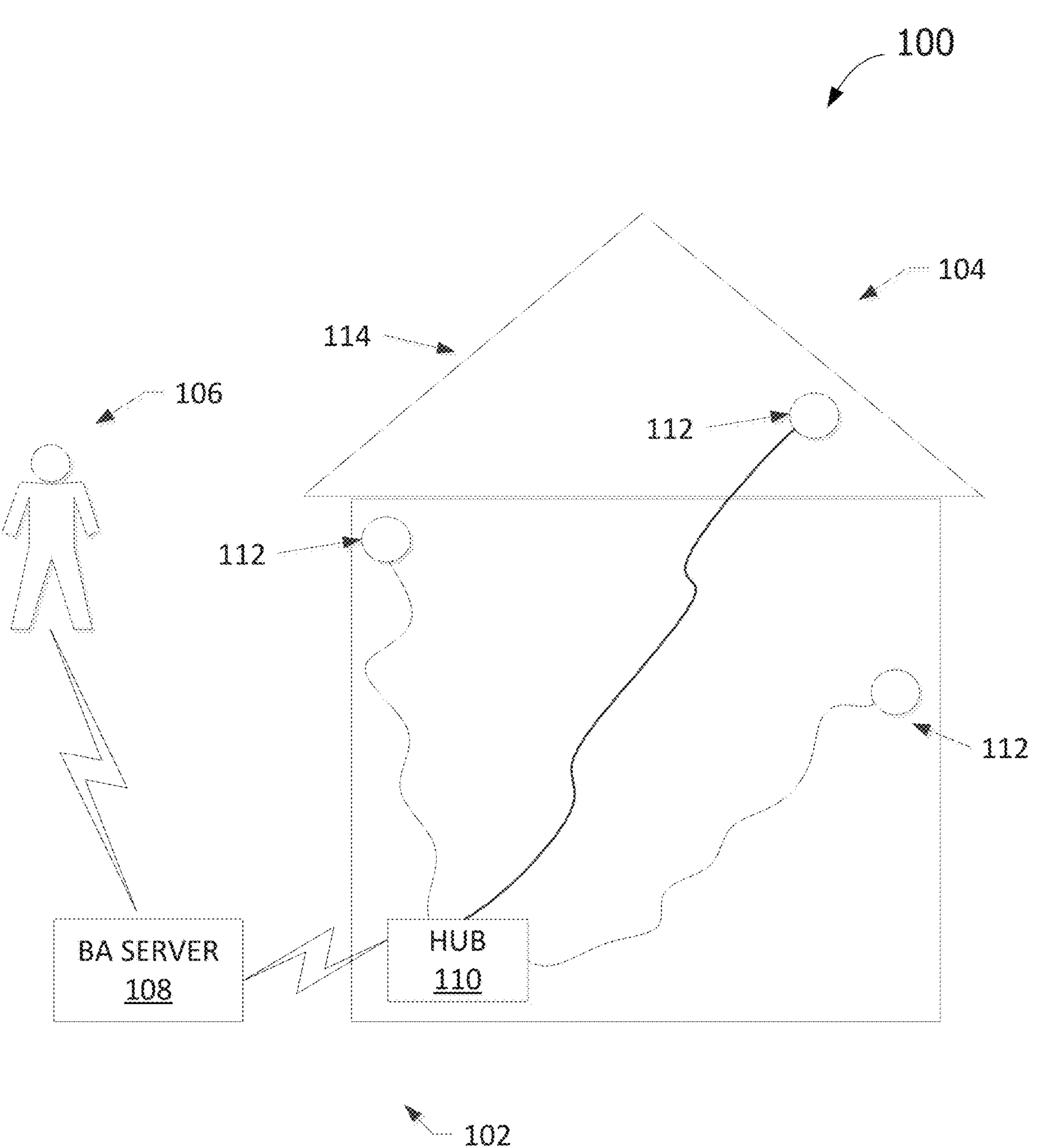
FIG. 1 illustrates an exemplary building environment in which a building analysis (BA) system monitors a building, such as a residential home of a building owner ("homeowner")

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION OF THE DRAWINGS

The present embodiments may relate to, inter alia, systems and methods for identifying symptoms through sensor data characteristics trend analysis, and taking corrective actions and generating recommendations. Given an environment and context in which a sensor or set of sensors is installed, the present embodiments may identify events to which readings are attributable. From such events, a computer system, such as the BA system discussed herein, may determine a set of characteristics which are applicable to the event. The computer system may continue to monitor similar events over time, recording the key characteristics such that trends in the characteristics can be identified and compared with similar trends that can be associated with known conditions which could affect the entity or entities involved with the event.

One concrete example which solidifies the concept with specific terms may include: Given a home in which a microphone is installed, the computer system may identify sounds consistent with toilet flush events and the sound of a toilet tank filling. Characteristics of the event might include duration of flush (flap open to flap closed), duration of tank fill, presence of a tank fill event with/without a flush event. Certain trends over time could be observable by the computer system from these characteristics-including leaky seals or valves, mineral buildup in water lines, slipping floats, etc. Imperceptible changes in fill duration over a short interval may be more noticeable by the computer system over a longer sample.

Another example may include: Given a home where a microphone is installed, the computer system may identify human cough events. Characteristics of the event might include pitch, which could identify an individual (anonymous), phlegminess, a perceived wheeze, repetitions within a given interval, duration of a cough, etc. The computer system may monitor characteristics over time, such that known patterns of certain conditions or illnesses can be identified as early as possible.

Another example may include: Given a home in which a thermometer and a microphone are installed, and for which current outdoor weather conditions are known, the computer system may monitor relevant sounds such as: whistling noises consistent with leaky windows; air conditioner/heater turning on/off; high pitched noises developing, indicative of fan becoming unbalanced, bearings going out, jets becoming clogged, etc.; and/or muffled outdoor noises becoming clear indicative of an open door or window. The computer system may monitor relative indoor/outdoor temperature differential over time in context of conditions and events, and/or look for symptoms consistent with dirty filters, degrading door/window seals, losses in efficiency due to maintenance issues. The computer system may include and/or be in wired or wireless communication with various types of sensors, such as cameras capable of various spectrums (visible, thermal, infrared, etc.); microphones; thermometers; gas/particle detectors (Carbon Dioxide, Carbon Monoxide, Smoke, Allergens, Oxygen detectors/sensors); light sensors; and/or vibration sensors, and/or accelerometers.

Other applications of the concept in the context of a home with lots of sensors installed may exist, with some monitoring intervals being short others long. For instance, the computer system may be configured to listen for sound of water heater kicking on, correlated with sounds of showers, baths, dishwashers, etc., and watch for trends indicating that water heater might be going out, becoming inefficient, etc.

The computer system may be configured to listen for sound of sump pump kicking on, correlate that over time with average rainfall, current weather conditions, weather conditions over the last few days, possible snow melt. Obtain data about HP and pumping capacity from user to make calculations about how much water is being pumped out, etc. The computer system may be configured to suggest float adjustments, or suggest checking for leaky check valves, etc. The computer system may be configured to notice that based upon similar water conditions, that the sump or other pump should be running and isn't (even though power is clearly on). The computer system may be configured to suggest the development of leaks in a home foundation, possible surrounding terrain drainage issues, etc.

The computer system may be configured to listen and smell for natural gas in kitchen, and recall whether a lighter was ever initiated. The computer system may be configured to detect minute temperature increase that would be indicative of lit burners—if the system determines that the gas is on the stove but is not lit, it may generate an alert.

The computer system may be configured to listen and/or monitor for electrical buzzing, arcing, etc. The computer system may be configured to sense odors (e.g., smells) associated with burning insulation and building fires by utilizing sensors, such as for example, metal oxide based semiconductor sensors, gas detection sensors (e.g., hydrogen sensors), infrared cameras, and/or temperature sensors. If the system detects burning insulation, the system may generate an alert.

The computer system may be configured to listen for cooling fans on computers kicking on and note frequency, duration and strength. The system may sense trends indicating dusty fan grates, and/or sense temperatures in areas and make correlations to overheating equipment.

The computer system may be configured to detect dimming of lights due to inductive loads coming online, listen for sounds, correlate and look for potential issues. The computer system may detect dimming of lights in areas with light fixtures, and suggest changing bulbs. If camera enabled, the system may take pictures of light fixtures at different light intensities and analyze photos to corroborate. The system may also keep an inventory of fixtures, such as bulbs that need replacement, and present alerts to a user (e.g., homeowner) at a time of failure detection. Additionally or alternatively, the system may present a list of fixtures needing replacement and/or attention upon receiving a request from the user.

Sensors may record home conditions over a period of time or continuously. For instance, sensor data may be captured or collected once a day or week, or continuously. Random sampling of the sensor data may also be performed by the computer system. The computer system may analyze the sensor data to track trends, identify problems and changes in state over time.

For instance, the computer system may identify abnormal noises within a home, such as grinding noises or changes in running water (e.g., a toilet running changes from 3 seconds to 5 seconds). The computer system may identify noise changes over time that are associated with air pressure or sounds. A microphone integrated with the computer system may, for example, collect data to detect when a furnace, air conditioning unit, and/or sump pump turns on and off. The microphone may also collect data that reveals bad seals in windows or door from whistling. Other sensors may detect abnormal temperature gradients around doors or windows—indicating bad seals that should be replaced or repaired.

The computer system may also identify issues or problems with paint or siding, such as via digital image analysis. The computer system may also monitor and analyze air quality within the home. The sensor data may be used to develop a risk profile for a home, which in turn may be used in generating a home loan quote or a homeowner's insurance quote for the home.

In one embodiment, a machine learning algorithm or program may develop a baseline rating model for a home. New sensor data may be analyzed by the computer system to identify events, and then determine appropriate corrective actions and/or recommendations. If the corrective actions or recommendations are implemented, a homeowner's insurance discount may be increased to facilitate encouraging risk averse behavior by homeowners. In some embodiments, the computer system may execute (e.g., direct or carry out) the recommended action on behalf of the homeowner to mitigate and/or prevent damage to the building, and to prevent the identified event(s) from injuring a building occupant.

The sensor data may also be used to generate usage-based insurance (UBI) for a home, such as insurance for a given amount of time (e.g., a week or month). The sensor data may be used to more accurately determine risk for the home during the homeowners UBI time period.

Exemplary Building Analysis System & Server

The present embodiments may relate to, inter alia, systems and methods for detecting building events and trends. In one exemplary embodiment, the methods may be performed by a building analysis (BA) server.

In the exemplary embodiment, a building analysis (BA) system may monitor a building, such as a residential home of a homeowner. The BA system may include a building analysis (BA) server. The BA server is a remote server, and is in communication with a hub and a user (e.g., homeowner, building owner). The hub may be located within the building and/or otherwise positioned in proximity of the building's premises. The hub is configured to receive data related to infrastructures from a plurality of sensors within the building. The hub transmits received data to the BA server for analysis.

In the exemplary embodiment, the BA server is configured to analyze data received from the hub to detect events and identify trends related to infrastructures being monitored by the BA server. The BA server may identify trends by determining correlations between detected events. "Events" as used herein may refer to occurrences (e.g., incidents) that take place within the building or on the building's premises. More specifically, "events" refer to occurrences that are associated with infrastructures being monitored by the BA server. Infrastructures may be registered with the BA server by a user. For example, a homeowner may register his or her home for monitoring by BA server. During the registration process, the homeowner may register each infrastructure that is within or otherwise associated with the home. The BA server may create an inventory of all the infrastructures associated with the home that are registered for monitoring by the BA server. In the exemplary embodiment, the BA server creates an infrastructure profile for each infrastructure registered for monitoring.

In the exemplary embodiment, infrastructures are associated with a particular building that is registered for monitoring by the BA server. "Infrastructures," as used herein, refers to a (i) fixture included within or part of the building, and/or (ii) person(s) located within the building. "Fixtures" may refer to items within a building (e.g., electronic devices, appliances, water heater, air conditioner, furnace), building materials (e.g., materials associated with a building's pipes, roof, walls (exterior and interior), flooring), zones of a building's premises (e.g., rooms, garage, hallway, attic, basement, patio, backyard), and items associated with the building and/or the building owner, such as vehicles (e.g., homeowner's vehicle). "Persons" may refer to building residents, such as an individual (e.g., homeowner) or a group of residents (e.g., a family, roommates). During the building registration process, each fixture and/or person(s) associated with the building may be identified and registered for monitoring by the BA server.

Infrastructure profiles may be generated by collecting data samples over a period of time for each registered infrastructure. The samples may be analyzed to determine a condition of a monitored infrastructure (e.g., a building's roof). In some embodiments, an infrastructure profile of an infrastructure is compared to an optimal profile for the infrastructure to detect an event and/or trend associated with the infrastructure. In other embodiments, samples from different time periods may be compared with one another to detect events and/or trends associated with an infrastructure. For example, the BA server may compare pipe sounds received at the beginning of a week to pipe sounds received at the end of the week to determine that humming sounds from the building's bathroom pipes have gradually continued to get louder and louder. In this example, the BA server may compare data from the pipe's infrastructure profile to an optimal profile generated for the pipe to detect a problem with the bathroom pipes.

In the exemplary embodiment, an optimal profile is generated for each registered infrastructure. Optimal profiles may include characteristics representative of an optimal and/or standard condition (e.g., reference parameters, reference conditions) for the infrastructure being monitored. In some embodiments, an optimal profile for an infrastructure may include characteristics of normal operating conditions, such as sounds, operating frequency, energy consumption, and efficiency levels associated with the infrastructure.

In embodiments where the infrastructure to be monitored is a person, the optimal profile may include characteristics representative of how the person normally sounds, looks, and/or acts. For example, in an optimal profile for a homeowner, the optimal profile may include samples of the person's voice or appearance obtained during registration. For example, if a homeowner is registering himself as an infrastructure to be monitored, the BA server may request that a sample of the homeowner's voice be provided. In another example, the BA server may request that a photo of the homeowner's face be provided. Accordingly, the BA server may receive samples specific to characteristics of the homeowner to enable the BA server to accurately identify and monitor the homeowner.

In some embodiments, the BA server may generate an inventory, such as a sensor inventory, that identifies all the sensors that are in communication with a specific hub. The inventory may include a map that identifies the locations of each sensor within or around the building. The inventory may include a list of sensor identifiers, and may further identify the types of sensors being used within a building.

In the exemplary embodiment, the BA server monitors building infrastructures to identify building events and to predict building patterns (e.g., trends). The BA server may find correlations between identified events to detect trends for one or more infrastructures of the building. For example, the BA server may be configured to detect minute temperature changes in a home's electrical wiring system that are indicative of a high probability of overheating if not addressed promptly. Accordingly, rather than waiting before an overheating event occurs, such as a fire, the BA server may detect building compromises ahead of time, and enable a homeowner to take preventative action to prevent serious and costly building failures.

In further embodiments, the building may include a response device that is in communication with the BA server. In these embodiments, the BA server may be configured to automatically deploy a response device to address a detected event. The response device may be a portable sensing device. In some embodiments, the response device may be a robotic arm, or a robot with one or more robotic arms. The robotic arm and/or robot may be static (e.g., fixed). Additionally or alternatively, the robotic arm and/or robot may be mobile. The response device may be configured to take corrective action on behalf of a homeowner, such as unplugging a hair iron that has been left on in the bathroom. In other embodiments, the BA server may instruct the response device to collect additional data regarding a detected event. For example, the BA server may dispatch alerts to one or more response devices that are capable of taking corrective action on behalf of the homeowner.

In the exemplary embodiment, the BA server is configured to generate recommendations based upon the detected events and trends. The BA server may recommend corrective and/or preventative actions to be taken by the homeowner. For example, the BA server may recommend that a homeowner replace dirty filters or address detected leaks in the building's foundation. In some embodiments, the BA server may provide the homeowner with third-party contact information, such as that of a nearby contractor or technician to address the detected event.

In further embodiments, the BA server may recommend that the homeowner seek medical attention based upon analyzed sensor data. In these embodiments, the BA server may determine that the homeowner is displaying cold or flu symptoms. For example, the BA server may detect, from audio and/or camera data of a homeowner, data indicative of coughs, sneezes, and a runny nose. Based upon the duration and severity of the detected symptoms, the BA server may recommend that the homeowner visit a medical professional.

In another embodiment, the BA server may recommend that a homeowner enroll in a savings plan (e.g., savings fund) to finance future home repairs and maintenance projects. In these embodiments, the BA server may compare samples from an infrastructure profile for a monitored infrastructure to a corresponding optimal profile that includes reference parameters representative of optimal operating conditions for the infrastructure. Based upon these comparisons, the BA server may generate a maintenance timeline for the infrastructure and estimate a cost of repair for each maintenance event.

For example, the BA server may recommend, based upon initial conditions detected for a building's heating, ventilation, and air condition (HVAC) system, that a full replacement of the HVAC system is needed in 5 years. The BA server may estimate costs for replacing and installing new HVAC units from reputable contractors to be at least ten thousand dollars. Accordingly, the BA server may calculate an estimated amount (or range) of money that should be set aside each month and/or each year to budget costs associated with replacing the full HVAC system. The BA server may provide the savings plan to the homeowner, and recommend that the homeowner enroll in the savings plan to defer a designated amount of his or her paycheck into a savings fund maintained by the BA server each month.

In the exemplary embodiment, the BA server may be configured to monitor multiple buildings. The BA server may detect correlations between events and trends for multiple buildings to identify trends that affect a geographical area, such as a neighborhood. For example, the BA server may be able to identify a power line failure upon analyzing electricity data for homes in a neighborhood. In another example, the BA server may identify a trend of utility failures due to a specific utility equipment, such as frequent power outages in buildings that are serviced by one utility equipment. In the exemplary embodiment, the BA server is configured to transmit support data (e.g., an analysis of detected events and trends for one or more buildings) to third party companies, such as utility companies.

The BA server may generate a record of all of the recommendations provided to a homeowner for a specific building. The record may indicate, for each provided recommendation, whether the recommendation was accepted (e.g., followed) or denied (e.g., ignored) by the homeowner. The BA server may track how many recommendations were followed. In some embodiments, recommendations may be categorized by priority level (e.g., urgent, high, medium, or low).

The BA server may generate a lifestyle credit rating for the homeowner based upon homeowner behavior with respect to the provided recommendations. The BA server may take into consideration a responsiveness level of the homeowner with respect to the provided recommendations. The lifestyle credit rating may be based upon factors, such as a total number of accepted recommendations and a total number of corrective and/or preventative actions taken by the homeowner within a given period of time. The BA server may update the lifestyle credit rating on a periodic basis. The lifestyle credit rating may be used by the BA server to offer incentives to the homeowner, such as a discount in the homeowner's insurance premiums, a credit, and/or quotes for life insurance and/or automobile insurance policies.

Properties registered for monitoring by the BA server may include multi-building and/or multi-residential properties, such as apartment buildings, high-rise condominiums, hospitals, and/or office properties. In these embodiments, all of the monitoring services available to a homeowner user, as described herein, may not be available to users who manage these multi-residential/multi-occupant properties. For example, a property manager user registering an apartment complex for monitoring by the BA server may not opt in to receive lifestyle credit ratings or to enroll in a maintenance savings account. In other embodiments, monitoring services specific to homeowner users may not be available to users who are registering multi-residential properties for monitoring by the BA server. In these embodiments, these users may register a multi-residential building complex for monitoring by the BA server to preemptively notify residents, a landlord, and/or a building maintenance team of corrective actions that can be taken to minimize exposure to building damage, and to protect the health and safety of building occupants.

Accordingly, the systems and methods described herein address at least these problems. Specifically, the systems and methods described herein may be implemented using computer programming or engineering techniques including computer software, firmware, hardware, or any combination or subset thereof, wherein the technical effects may be achieved by performing at least one of the following steps: (i) receiving, from a plurality of sensors within a building, sensor data related to a condition of an infrastructure, the infrastructure being at least one of a fixture and/or at least one person located within the building; (ii) analyzing the sensor data to identify the infrastructure; (iii) applying a prediction model to the sensor data to detect an event associated with the infrastructure; (iv) generating a recommendation based upon the detected event, and (v) transmitting the recommendation to a user computing device associated with a building owner.

Exemplary technical effects of the systems, methods, and computer-readable media described herein may include, for example: (i) detecting building system failures before additional or ancillary damage is caused by the failure; (ii) detecting minute changes that are indicative of potential building system failures by identifying correlations between detected events; (iii) identifying correlations that affect multiple buildings to detect overarching trends; (iv) detecting certain types of system failures such as, for example, deterioration of insulation performance over long periods of time; (v) tracking historical records of a building's health and improvements made to the building over time; (vi) automatically deploying a response device to take corrective action on behalf of a homeowner, (vii) increasing the amount and quality of information collected for a building, (viii) improving the accuracy of insurance models (e.g., underwriting and/or actuarial models) used to make insurance decisions; and/or (ix) continuously improving the accuracy of data used to make insurance decisions.

Exemplary System for Detecting Building Health Trends

FIG. 1 illustrates an exemplary building environment 100 in which a building analysis (BA) system 102 monitors a building 104, such as a residential home of a building owner ("homeowner") 106. In the exemplary embodiment, BA system 102 may include a building analysis (BA) server 108

(e.g., remote from or local to building 104 premises), a hub 110 configured to transmit sensor data and to receive commands from BA server 108, and/or a plurality of sensors 112 deployed (and/or embedded) throughout building 104. Each sensor 112 may provide sensor data to hub 110 within building 104.

Figure 4:
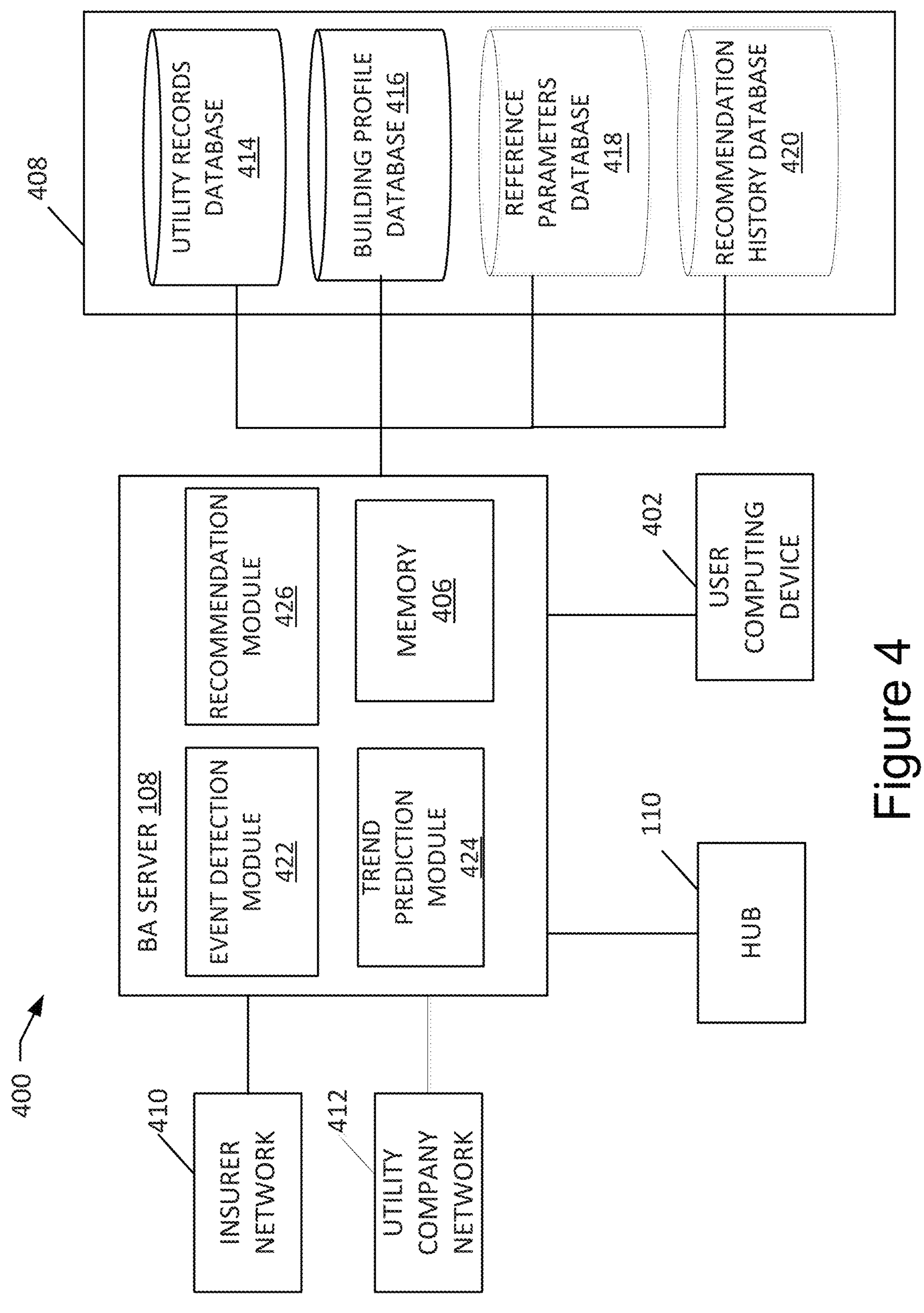
FIG. 4 illustrates a simplified block diagram of an exemplary computer system for implementing a computer-implemented process, in accordance with one embodiment of the present disclosure.

Hub 110 may be in communication with BA server 108, which may perform various data analysis and storage, and may include a user interface that allows homeowner 106 to view alert messages from BA server 108. Additionally or alternatively, the user interface may allow homeowner 106 to see data and analytics about the health of building 104. In further embodiments, BA server 108 may be in communication with a user computing device (such as user computing device 402 as shown in FIG. 4) associated with homeowner 106. In these embodiments, BA server 108 may transmit alert messages directly to the user computing device.

Sensors 112 may be in wired communication with hub 110. In other embodiments, some sensors 112 may be in wireless communication with hub 110 (e.g., via an IEEE 802.11 wireless local area network). In still other embodiments, sensor data may be stored local to sensor 112 and transferred or collected from sensor 112 and transferred to hub 110 and/or BA server 108. Further, in the example embodiment, some sensors 112 may be locally powered (e.g., battery, direct-attached solar array), other sensors 112 may be powered via connection to a power distribution network (e.g., 120 Volt Alternating Current network of building 104), and still other sensors 112 may not require power or otherwise self-powered. In some embodiments, multiple hubs 110 may be implemented in building 104. For example, multiple hubs 110 may be implemented due to various sensor requirements for wiring. In other embodiments, sensor aggregators may report to one hub 110 (e.g., a central hub).

During operation, output values from sensors 112 are received by hub 110 and transmitted to BA server 108 for storage in a memory (such as memory 406 as shown in FIG. 4) and for analytics and further processing, as described below.

In the exemplary embodiment, building analysis (BA) system 102 may be configured to monitor and collect sensor data with respect to one or more infrastructures associated with building 104. As used herein, the term “infrastructure” is used to refer to a (i) fixture included within or part of building 104 and (ii) person(s) located within or otherwise associated with building 104. Fixtures may contribute to providing one or more functions provided by or associated with the building. Fixtures may include structural components (e.g., building materials), home devices, such as electronic devices used in building 104, electronic appliances (e.g., washer and dryer), or zones (e.g., a room or hallway) associated with building’s 104 premises.

In the exemplary embodiment, sensors 112 may be located throughout building 104. Sensors 112 may be embedded throughout roofing material of building 104 to monitor a rooftop 114. Sensors 112 may also be embedded throughout construction materials of building 104 of both the interior and exterior of building 104 to monitor the condition of structural components. Sensors 112 may also be positioned in different zones (e.g., rooms, hallways) throughout and around building 104, such as in a basement, foundation, attic, room, or driveway of building 104. In the exemplary embodiment, sensors 112 provide data that may be used by BA server 108 to monitor the health (e.g., condition) of one or more infrastructures associated with building 104 and identify events.

Sensors 112 installed in or used in association with building 104 may include, but are not limited to, imaging devices, cameras (e.g., 2D and 3D cameras, such as thermal infrared cameras), audio recorders (e.g., microphones), acoustic sensors, temperature sensors (e.g., wireless thermometer sensors), humidity sensors, air particle sensors (e.g., light scattering particle sensors, infrared sensors) for detecting airborne particles and gas, such as carbon dioxide, carbon monoxide, smoke, allergens, dust, and mold, motion sensors, light sensors (e.g., sensors for automatically controlling lighting), heat sensors (e.g., sensors that measure the thermal radiation emitted by an object), and vibration/accelerometer sensors.

In the exemplary embodiment, BA system 102 may be configured to collect sensor data from sensors 112 to identify building events and to detect patterns (e.g., trends). BA system 102 may be configured to monitor registered infrastructures for failure of, or other compromise of, one or more functions associated with one or more building components. For example, a failure or compromise of rooftop 114 may mean that water has been allowed to leak through the shingles and underlayment, and perhaps through the deck surface boards and into the interior of building 104. Such a failure of the roofing system may lead to, for example, water or mold damage to the deck surface board(s) and/or to other interior components of building 104. In the exemplary embodiment, BA system 102 may also be configured to monitor for potential failures or compromises of one or more functions associated with the building components.

Figure 2:
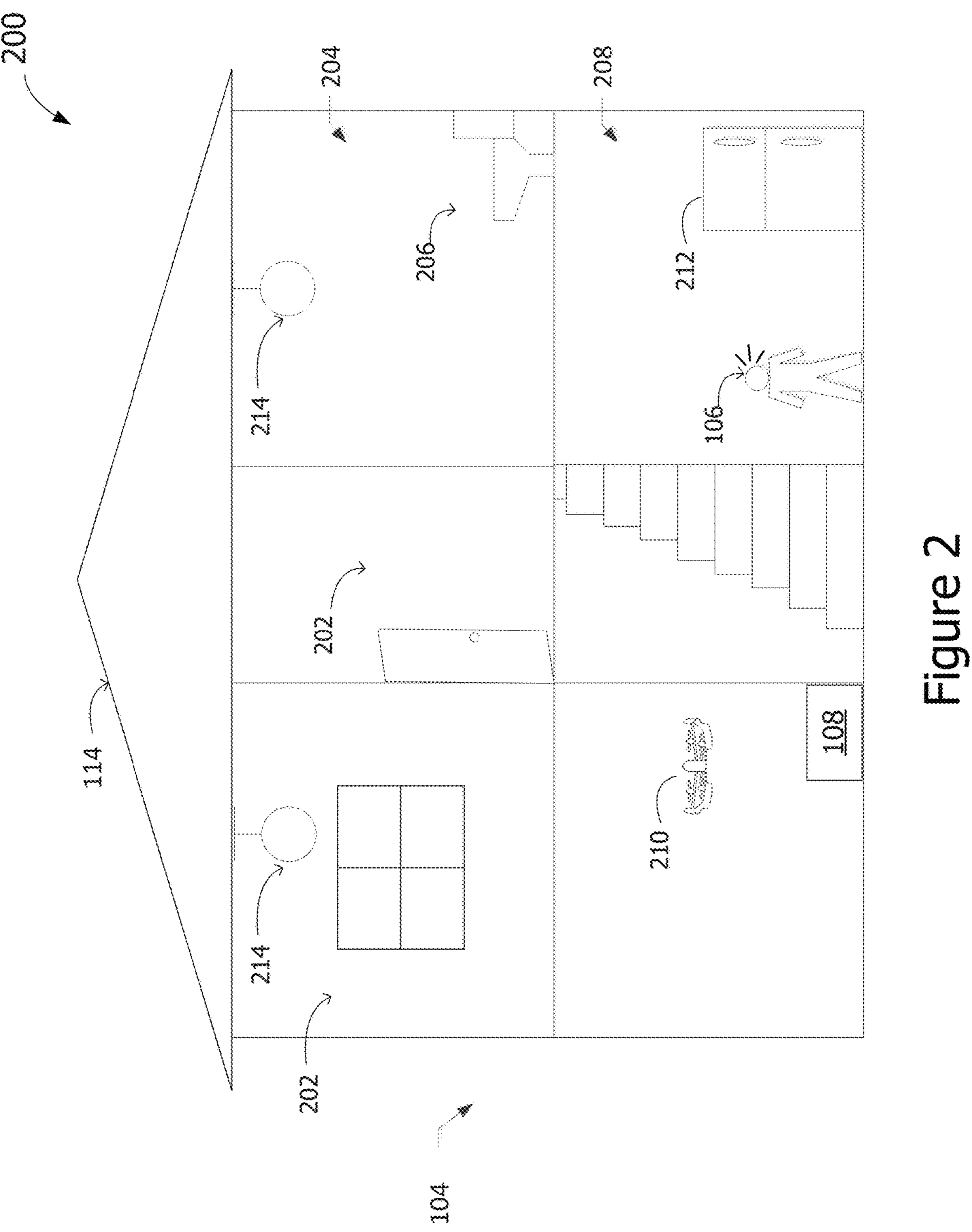
FIG. 2 illustrates a cross section side view of an exemplary building that may be monitored by the system shown in FIG. 1 to detect and respond to events within the building.

FIG. 2 illustrates a cross section side view 200 of an exemplary building, such as building 104, which may be monitored by building analysis (BA) system 102 (both shown in FIG. 1) to detect and respond to events and trends associated with building 104. Building 104 may be divided into a plurality of zones 202. Each zone 202 may be a separate room or hallway within building 104.

In the exemplary embodiment, sensors 112 may be placed throughout each zone 202 to monitor one or more registered infrastructure of building 104. Sensors 112 may be stationary. For example, sensors 112 may be positioned at fixed locations throughout building 104 to monitor a particular zone 202, fixture, and/or building component. In the exemplary embodiment, sensor 112 may be a microphone installed in a bathroom 204. Sensor 112 may be installed near, on, or within a toilet 206, and may be configured to monitor water sounds consistent with flushing and refilling a toilet tank. Sensor 112 may also be configured to monitor sounds associated with each part of the toilet, such as valves, tubes, flappers, and water pipes. For example, sensor 112 may be configured to collect audio data in bathroom 204, and transmit the collected data to hub 110. In this embodiment, BA server 108 may receive the collected sensor data from hub 110, and analyze the data to identify characteristics consistent with normal flush events.

BA server 108 may be able to analyze sensor data and identify events and trends that deviate from characteristics associated with normal operating events for an infrastructure. For an infrastructure, such as toilet 206, BA server 108 may identify characteristics, such as a duration of a flush (e.g., flap open to flap closed), a duration of a tank fill, and/or audio data (e.g., sound data) associated with a tank fill to detect failures or potential compromises. For example, BA server 108 may detect, from audio data, sounds associated with a toilet tank filling with water, but also detect the absence of sounds associated with flushing toilet 206. In this example, BA server 108 may determine that toilet 206 is not functioning properly.

BA server 108 may also be configured to detect, from the collected sensor data, a hissing sound or a water resonance sound, and determine that a fill valve of the toilet is not functioning properly. In another example, BA server 108 may detect, over a given period of time, that a toilet tank is gradually taking longer to fill. In another example, BA server 108 may detect sounds from the main pipe consistent with sediment buildup from the collected sensor data. Over time, BA server 108 may identify characteristics, including leaky seals, leaky valves, mineral buildup in water lines, and slipping floats.

BA server 108 may compare samples of sensor data to historic sensor data collected for a fixture, such as toilet 206, to detect trends. For example, BA server 108 may compare a sensor data sample for a given day to sensor data collected over a specific period of time to identify patterns or deviations from collected sensor data. BA server 108 may also compare sensor data to an optimal profile to determine whether a specific sample is consistent with or deviates from the optimal profile. The optimal profile may include reference parameters representative of optimal conditions for a fixture.

In the exemplary embodiment, different types of sensors 112 may be used to monitor a given infrastructure. For example, building 104 may include cameras and energy sensors configured to monitor energy consumption within building 104, such as current sensors or smart meters. Cameras may be configured to monitor zones 202 of building 104 by continuously or periodically taking pictures of registered light fixtures, such as light fixtures 214. In this example, based upon the data from the cameras and the energy sensors, BA server 108 may detect that light bulbs for a specific light fixture burn out more frequently than light bulbs for other light fixtures in building 104. BA server 108 may analyze sensor data from multiple sensors, such as cameras, energy sensors, and audio sensors to detect an electricity problem or a problem with the light fixture itself. BA server 108 may detect, from analyzing data from multiple sensors, the gradual dimming of light bulbs for a specific light fixture. BA server 108 may further analyze photos from cameras showing different light intensities of the given light fixture over a period of time to determine that one or more light bulbs for the given light fixture need to be replaced.

In further embodiments, BA server 108 may be configured to detect the presence of gas. BA server 108 may utilize a variety of sensor types to detect the presence of gas in zones 202, such as a kitchen 208. For example, BA server 108 may analyze data from audio sensors in kitchen 208 to detect sounds associated with lighting a gas burner. BA server 108 may also analyze data from heat sensors to detect minute temperature increases that may be indicative of a lighted burner. BA server 108 may also analyze data from air particle sensors to detect the presence of gas in kitchen 208. By analyzing different types of sensor data from a plurality of sensors 112, BA server 108 may detect multiple events within building 104 with greater accuracy.

In some embodiments, hub 110 may be in communication with electronic devices that are equipped with sensors. In certain embodiments, BA server 108 may directly be in communication with one or more electronic devices. BA server 108 may identify devices within building 104 that consume the most energy by analyzing data from multiple sources (e.g., sensors, electronic appliances, utility meter readings). For example, BA server 108 may analyze data from energy sensors as well as data from audio sensors that monitor the sounds associated with each electronic device to monitor energy consumption.

In addition to sensors 112 positioned at fixed locations, building 104 may also include portable sensing devices, such as portable sensing device 210, that travel from zone 202 to zone 202 within building 104 to collect data as to one or more infrastructures. Portable sensing device 210 may be an autonomous drone that flies or otherwise moves about building 104 to collect sensor data from sensors 112 mounted on the autonomous drone. In some embodiments, portable sensing device 210 may be a robotic device equipped with sensors 112 and configured to collect data by traveling through building 104 on the ground, such as a land-based rover or drone configured to move about building 104.

BA server 108 may instruct hub 110 to deploy portable sensing device 210 from a charging station (e.g., dock) and travel from zone 202 to zone 202 to collect data. BA server 108 may instruct portable sensing device 210 to collect data based upon a predetermined schedule (e.g., every day at a specific time). In other embodiments, portable sensing device 210 may be deployed in response to an event detected by BA server 108. For example, BA server 108 may detect a sound in a particular zone 202 and deploy portable sensing device 210 to zone 202 to collect additional data for further analysis.

In the exemplary embodiment, BA server 108 may be in communication with a response device (not shown). The response device may be within building 104, and may be configured to take corrective action on behalf of homeowner 106. For example, BA server 108 may detect, from collected sensor data, that (a) a refrigerator 212 door has been open for a duration that exceeds an optimal threshold duration and (b) no one is home. In this example, BA server 108 may instruct the response device to travel to the kitchen and close refrigerator 212 door. In some embodiments, BA server 108 may transmit instructions to hub 110, which in response may instruct the response device. In some embodiments, portable sensing device 210 may be the response device.

In the exemplary embodiment, BA server 108 is configured to identify and monitor sounds associated with one or more residents of building 104, such as homeowner 106. BA server 108 may have an optimal profile that includes reference audio sample(s) of a resident being monitored by BA server 108. For example, homeowner 106 may have provided a sample of his or her voice to BA server 108 during a registration process. The provided sample may be stored in the homeowner's optimal profile, and used to identify and recognize homeowner's 106 voice from collected audio data. Samples of homeowner's 106 voice may periodically be compared to the homeowner's 106 optimal profile to monitor changes in the homeowner's 106 voice. In one embodiment, BA server 108 may detect that homeowner 106 is within building 104 by comparing received audio data to the homeowner's 106 optimal profile.

In some embodiments, BA server 108 may build a machine learning model to detect homeowner's 106 voice. BA server 108 may utilize the reference sample of homeowner's 106 voice in the homeowner's 106 optimal profile as well as historic audio data for homeowner 106 in the homeowner's 106 infrastructure profile to detect patterns in homeowner's 106 voice. Over time, BA server 108 may be able to identify certain characteristics associated with homeowner's 106 voice. For example, BA server 108 may detect that the homeowner's 106 voice sounds different (e.g., higher or lower pitch and tone) at varying times of the day.

BA server 108 may detect the absence of homeowner's 106 voice at specific times throughout the day on given days (e.g., when homeowner 106 is at work), and analyze data collected from other sensors 112 in building 104 to determine homeowner 106 routines.

BA server 108 may identify sounds associated with medical conditions, such as, for example, a cold by continuously monitoring a resident, such as homeowner 106. For example, BA server 108 may compare received audio data to reference samples for cough sounds and sneeze sounds to detect that homeowner 106 has coughed or sneezed. BA server 108 may record each coughing or sneezing event in memory (such as memory 406, shown in FIG. 4). BA server 108 may also detect the duration and intensity of a cough and/or a sneeze, and track the frequency of coughs and sneezes over a period of time. BA server 108 may determine a pattern of escalating coughs and sneezes in a given time period and predict, based upon reference parameters, that homeowner 106 has a cold. BA server 108 may identify and track characteristics of homeowner's 106 voice, including pitch, tone, as well as sounds associated with phlegm and wheezes. The repetitions of sneezes and coughs within a given interval may be tracked and stored in memory 406.

Exemplary Building Analysis Computer System for a Neighborhood

Figure 3:
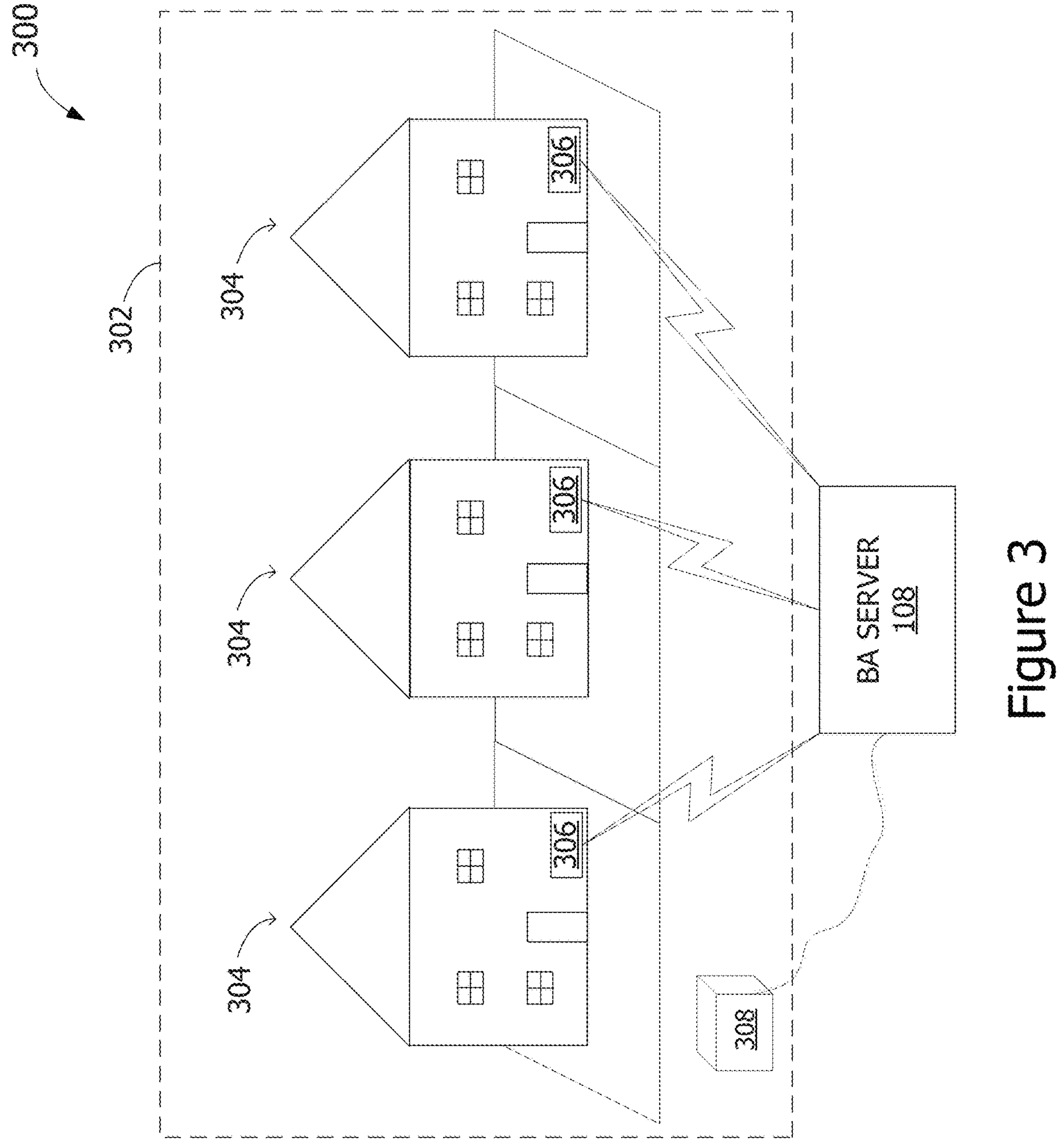
FIG. 3 illustrates an exemplary neighborhood that may be monitored by the system shown in FIG. 1 to detect events and trends that affect a plurality buildings within the neighborhood.

FIG. 3 depicts a side view 300 of a portion of an exemplary building analysis (BA) computer system 102 (shown in FIG. 1) for collecting sensor data from a neighborhood 302 (e.g., a coverage area) and detecting events and trends that affect neighborhood 302. Neighborhood 302 may be divided into a plurality of properties 304, such as building 104 (shown in FIG. 1). In the exemplary embodiment, each property 304 includes a hub 306 and a plurality of sensors, such as sensors 112 (shown in FIG. 1). Hub 306 may be similar to or the same as hub 110 (shown in FIG. 1). In the exemplary embodiment, BA server 108 may be in communication with hubs 306 as well as utility equipment 308. Utility equipment 308 may be configured to service properties 304 within neighborhood 302. Utility equipment 308 may be an electrical equipment utilized by an electrical company that provides power to properties 304 of neighborhood 302.

In the exemplary embodiment, BA server 108 is configured to collect sensor data from hubs 306, and identify events and correlations that affect more than one property 304. For example, BA server 108 may detect frequent power outages for properties 304 in neighborhood 302. BA server 108 may detect that the power outages occur at or near the same time for each affected property 304. BA server 108 may determine that the power outages are due to utility equipment 308. For example, BA server 108 may compare sensor data recently collected for utility equipment 308 to optimal operating parameters for utility equipment 308. From this comparison, BA server 108 may determine that utility equipment 308 is not operating properly. For example, BA server 108 may detect that utility equipment 308 has been damaged. Accordingly, BA server 108 may be able to determine that the power issue is not due to an electrical failure of one property 304, but is due to an external player (e.g., power company). In some embodiments, BA server 108 may be configured to transmit analyzed sensor data and/or detected events and trends to an external player, such as a power company responsible for utility equipment 308.

In the example embodiment, each property 304 is registered for monitoring by BA server 108. Users associated with each property 304 may opt-in for one or more of the monitoring services provided by BA server 108 described herein. Properties registered for monitoring by BA server 108 may include multi-building and/or multi-residential properties, such as apartment buildings, high-rise condominiums, hospitals, and/or office properties. In these embodiments, all of the monitoring services available to a homeowner may not be available to users who manage multi-residential properties.

Exemplary Building Analysis Computer System

Figure 7:
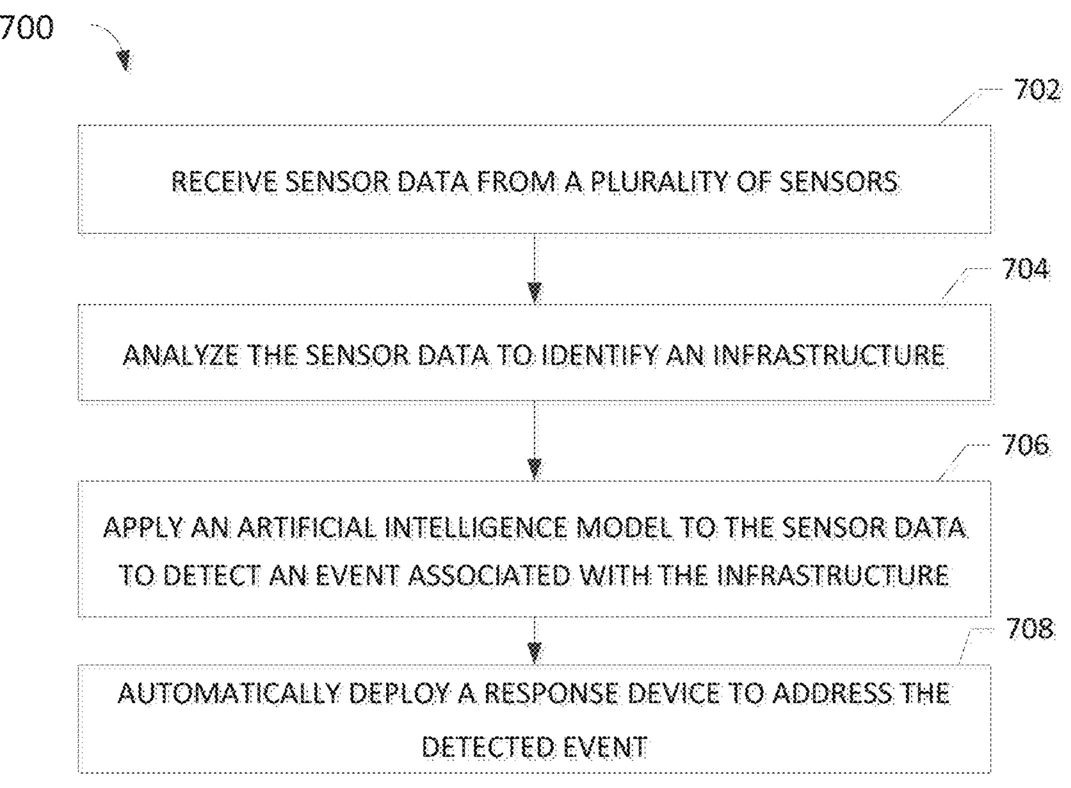
FIG. 7 illustrates a flow chart of an exemplary computer-implemented process 700 for automatically deploying a response device to address a detected event, in accordance with one aspect of the present disclosure.
Figure 8:
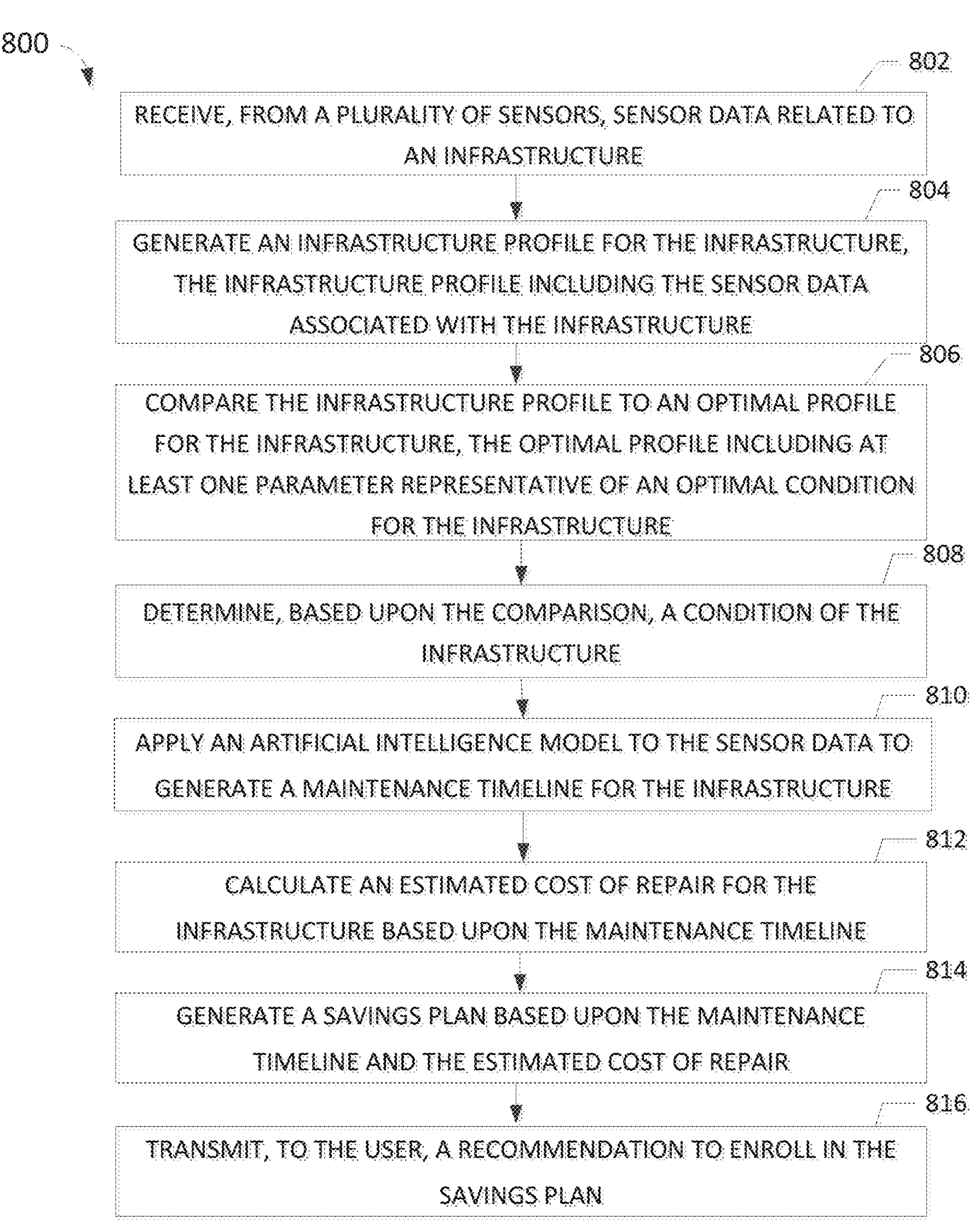
FIG. 8 illustrates a flow chart of an exemplary computer-implemented process 800 for generating a savings plan to finance future building repairs, in accordance with one aspect of the present disclosure.

FIG. 4 depicts a simplified block diagram of an exemplary computer system 400 for implementing a computer-implemented process, such as process 600 (shown in FIG. 6), process 700 (shown in FIG. 7) and process 800 (shown in FIG. 8). Computer system 400 may be similar to or the same as building analysis (BA) system 102 (shown in FIG. 1). In the exemplary embodiment, computer system 400 includes BA server 108 in communication with hub 110, user computing device 404, reference databases 408, insurer network 410 computing devices, and utility company network 412 computing devices. Reference databases 408 include a utility records database 414, a building profile database 416, a reference parameters database 418, and a recommendation history database 420. BA server 108 includes an event detection module 422, a trend prediction module 424, a recommendation module 426, and a memory 406.

BA server 108 may be configured to monitor a building, such as building 104 (shown in FIG. 1), by receiving sensor data from hub 110. In further embodiments, BA server 108 may be configured to receive sensor data for multiple buildings from a plurality of hubs, as illustrated by FIG. 3. Hubs 110 may be registered with BA server 108. BA server 108 may retrieve a building profile associated with a specific hub 110 from building profile database 416. For example, BA server 108 may receive a hub identifier from the sensor data, and utilize the hub identifier to retrieve a corresponding building profile from building profile database 416. Building profile database 416 may be configured to store building profiles for each building registered with BA server 108.

A building profile may include infrastructure profiles and optimal profiles associated with infrastructures (e.g., fixtures and/or person) registered for monitoring by BA server 108. A building profile may identify certain fixtures, such as electronic devices configured to securely communicate with BA server 108. Devices identified in the building profile may be registered with BA server 108, and may include hub 110, electronic devices, portable sensing devices (such as portable sensing device 210, shown in FIG. 2), and/or response devices. The building profile may further include an inventory of all sensors, such as sensors 112 (shown in FIG. 1) installed within building. The building profile for building 104 may include an inventory of all infrastructures being monitored by BA server 108. The building profile may include a virtual map of the interior and exterior of building 104. The map may identify sensor placements throughout building 104, hub 110 location in building 104, and the infrastructures being monitored (e.g., the location of each registered device).

In the exemplary embodiment, event detection module 422 of BA server 108 may detect building events based upon sensor data received from hub 110. Building events may include detected failures or compromises of fixtures, structural systems of building 104, or electronic devices. For example, detected building events may include burnt out light bulbs and dirty filters. Building events may also include potentially hazardous events detected by BA server 108, such as overheating equipment and the presence of gas, fires, and smoke. Building events may also include events, such as, but not limited to, opening and closing of doors and windows within building 104, and the coming and going of people between rooms of building 104. In one example, event detection module 422 may determine that a window has been opened by detecting, from received sensor data, muffled outdoor noises that become clear.

BA server 108 may retrieve reference parameters from reference parameters database 418 to generate optimal profiles for infrastructures, and detect building events using event detection module 422. Reference parameters database 418 may include reference samples for optimal operating conditions, sounds, and levels for the infrastructures being monitored by BA server 108. In some embodiments, reference parameters may include audio templates of homeowner's 106 voice. In further embodiments, BA server 108 may retrieve, from reference parameters database 418, prices, names, and contact information of contractors and/or technicians, and additional information to provide recommendations and estimates of repair costs.

In the exemplary embodiment, trend prediction module 424 of BA server 108 may recognize patterns (e.g., trends) based upon sensor data collected over a period of time. Event detection module 422 may detect events by analyzing samples of sensor data received from hub 110. Trend prediction module 424 may detect a correlation between detected events to predict trends for the infrastructures being monitored by BA server 108. Utility records for building 104 may be retrieved from utility records database 414 to assist in detecting trends. For example, collected sensor data may be compared to meter readings from utility records to identify deviations or patterns.

Trend prediction module 424 may also be configured to compare detected events and predicted trends for various infrastructures of building 104 to identify trends that would otherwise be difficult to detect. For example, BA server 108 may utilize trend prediction module 424 to correlate data from multiple infrastructure profiles to detect a trend. For example, BA server 108 may analyze sensor data associated with taking showers, running the dishwasher, and operating the laundry machine to determine that the water heater has been steadily operating at a lower efficiency level over time.

In the exemplary embodiment, recommendation module 426 of BA server 108 may generate recommendations based upon events detected by event detection module 422 and trends detected by trend prediction module 424. For example, upon detecting that the water heater is operating at a steadily lower efficiency level, recommendation module 426 may recommend that the water heater in building 104 be inspected by a technician as soon as possible to prevent serious failures from occurring. In the exemplary embodiment, recommendation module 426 recommends both preventative action and remedial action based upon the detected events and trends. For example, recommendation module 426 may recommend that homeowner 106 enroll in a home repair savings plan to finance future maintenance projects (e.g., repairing the roof). In another example, recommendation module 426 may recommend that homeowner 106 contact a plumber as soon as possible to inspect plumbing pipes that vibrate and rattle loudly upon flushing the toilet.

In the exemplary embodiment, BA server 108 is configured to save recommendations generated by recommendation module 426 and provided to homeowner 106 in memory 406. BA server 108 may be configured to generate a historical record of all recommendations accepted and denied by homeowner 106. Memory 406 may further include models (e.g., prediction models), generated from reference data (e.g., baseline data) and sample sensor data, that utilize artificial intelligence algorithms, including machine learning techniques for analyzing sensor data to detect events and trends. Memory 406 may also include raw sensor data received from hubs 110, detected events, and predicted trends for building 104.

In some embodiments, BA server 108 may be associated with, or part of a computer network associated with an insurance provider, such as insurer network 410. In other embodiments, BA server 108 may be in communication with insurer network 410 computer devices. BA server 108 may be configured to transmit, to insurer network 410, records of detected events and trends, provided recommendations, and a list of recommendations both accepted and denied (e.g., ignored) by homeowner 106. Computer devices of insurer network 410 may access these records to update and/or adjust an insurance policy of an insurance policy holder. In some embodiments, records may be used to update and/or create an underwriting model and/or an actuarial model to evaluate homeowner behavior.

In other embodiments, BA server 108 may be in communication with computer devices of one or more utility companies, such as utility company network 412. BA server 108 may be configured to transmit records of detected trends and events to computer devices of utility company network 412. For example, BA server 108 may identify a trend of frequent power outages that affect multiple buildings in an area (e.g., neighborhood). BA server 108 may detect that this is due to power line failures in the area, and may transmit support data to utility company network 412 to enable the utility company to address the problem.

Figure 5:
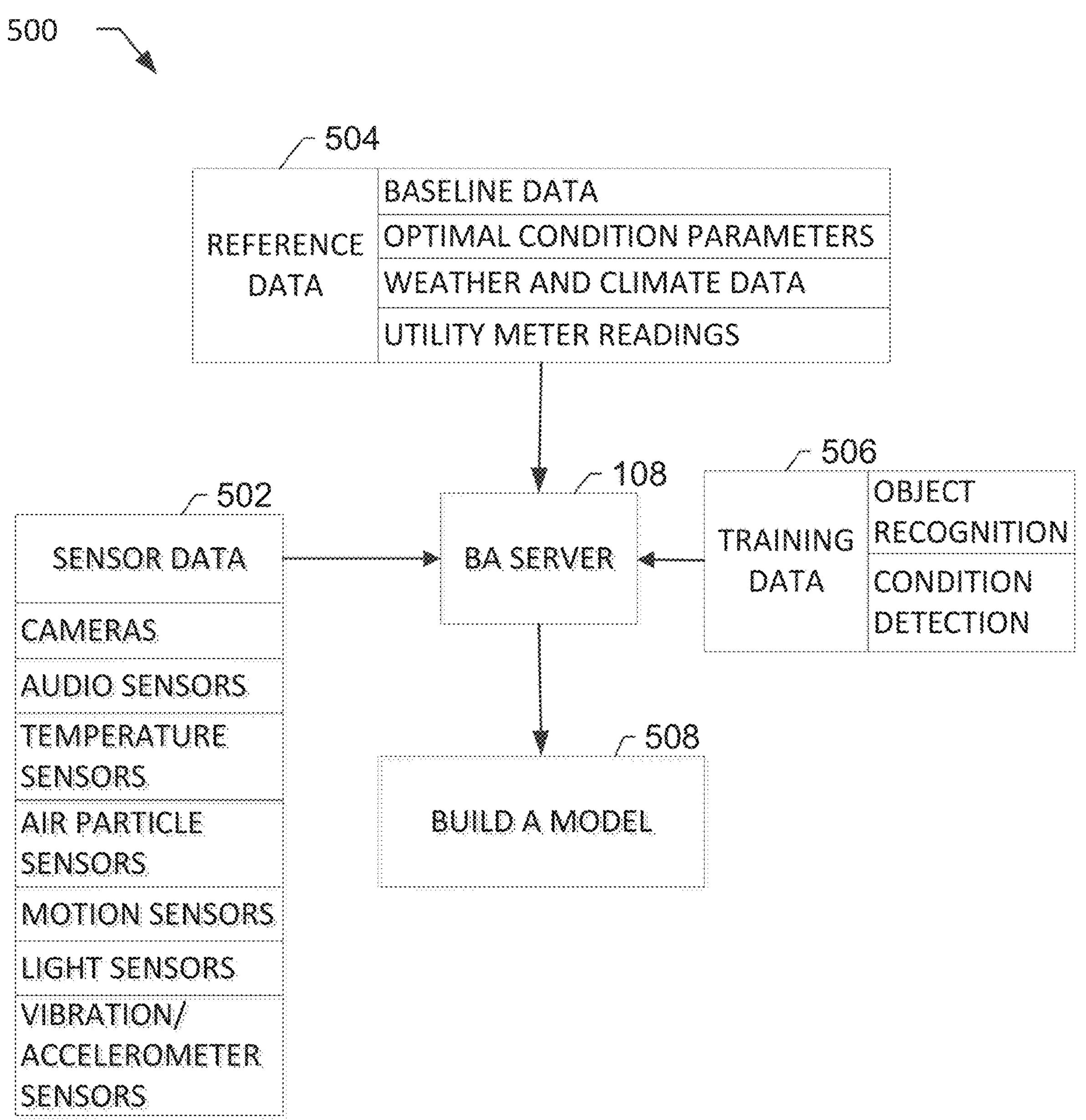
FIG. 5 illustrates a simplified block diagram of an exemplary process for building a model to detect building events and trends, in accordance with one embodiment of the present disclosure.

Exemplary Data Conversion Process for Building a Model to Detect Building Events and Trends FIG. 5 is a simplified block diagram 500 of an exemplary process using BA server 108 (shown in FIG. 1) for building 508 a model to detect building events and trends. In the exemplary embodiment, diagram 500 includes BA server 108, sensor data 502, reference data 504, and training data 506. In the exemplary embodiment, BA server 108 may build models for infrastructures being monitored by BA server 108.

In the exemplary embodiment, sensor data 502 includes data collected by a plurality of sensors, such as sensors 112 (shown in FIG. 1). More specifically, sensor data 502 includes data from different types of sensors that monitor a building, such as building 104 (shown in FIG. 1). Sensor data 502 may include data from cameras, audio sensors, temperature sensors, air particle sensors, motion sensors, light sensors, and vibration/accelerometer sensors. In the exemplary embodiment, BA server 108 analyzes data received from different types of sensors to detect events, and identify correlations between these events to predict trends associated with building 104. BA server 108 may receive sensor data 502 from hub 110 (shown in FIG. 1). In some embodiments, BA server 108 may directly receive sensor data 502 from one or more sensors monitoring building 104.

Reference data 504 may include baseline data (e.g., initially-collected data) for infrastructures that are monitored by BA server 108. Baseline data may include initial sample data received by BA server 108 when registering an infrastructure with BA server 108. For example, baseline data may be sample data taken of rooftop 114 (shown in FIG. 1) when homeowner 106 initially registers building 104 with BA server 108. In this example, baseline data for rooftop 114 may indicate an overall condition of rooftop 114, as well as conditions for specific areas of rooftop 114 at the time of registration. This enables BA server 108 to detect potential damages or problems with the rooftop.

Reference data 504 may also include optimal condition parameters and thresholds for the infrastructures being monitored by BA server 108. Optimal condition parameters may include acceptable levels of various airborne particles in a residential dwelling as well as normal operating conditions for infrastructures, such as sump pumps, water heaters, air conditioners, pipes, and electronic appliances. Reference data 504 may also include environmental data, such as weather conditions and climate data. Reference data 504 may further include utility meter readings for a building, such as building 104.

Training data 506 may include objection recognition and condition detection datasets. Training data 506 may include one or more sets of test data for each type of sensor utilized by BA server 108 in monitoring building 104. Training data 506 may be used to build a model that can detect events and identify patterns and correlations between and among the detected events. In some embodiments, training data 506 may include sample image data used to train a model to recognize various types of infrastructures, infrastructure conditions (e.g., damaged rooftop, dirty filters, leaky faucets), and events (e.g., an opened door or window). In other embodiments, training data 506 may include sample audio data that is used to train a model to recognize various types of sounds, such as sounds associated with leaky seals or valves, mineral buildup in water lines, cooling fans, leaky windows, sump pumps, electrical arcing, main hums (e.g., power line hum), and fan grates.

In the exemplary embodiment, BA server 108 uses the above-described datasets to build 508 one or more models to detect building events and identify trends. Models may implement article intelligence algorithms, such as a machine learning algorithms to predict events and patterns with increased accuracy. For example, BA server 108 may apply a model to a specific set of sensor data received for a sump pump over a period of time, and determine that it usually takes an expected range of time for the sump pump to turn on. BA server 108 may compare this detected range of time to optimal operating parameters for sump pumps to determine whether the sump pump is operating efficiently. In another example, BA server 108 may compare samples of sensor data for a period of time to historical data received for the sump pump, and detect that the sump pump is taking longer and longer to turn on and complete a cycle.

Exemplary Computer-Implemented Method for Generating a Recommendation

Figure 6:
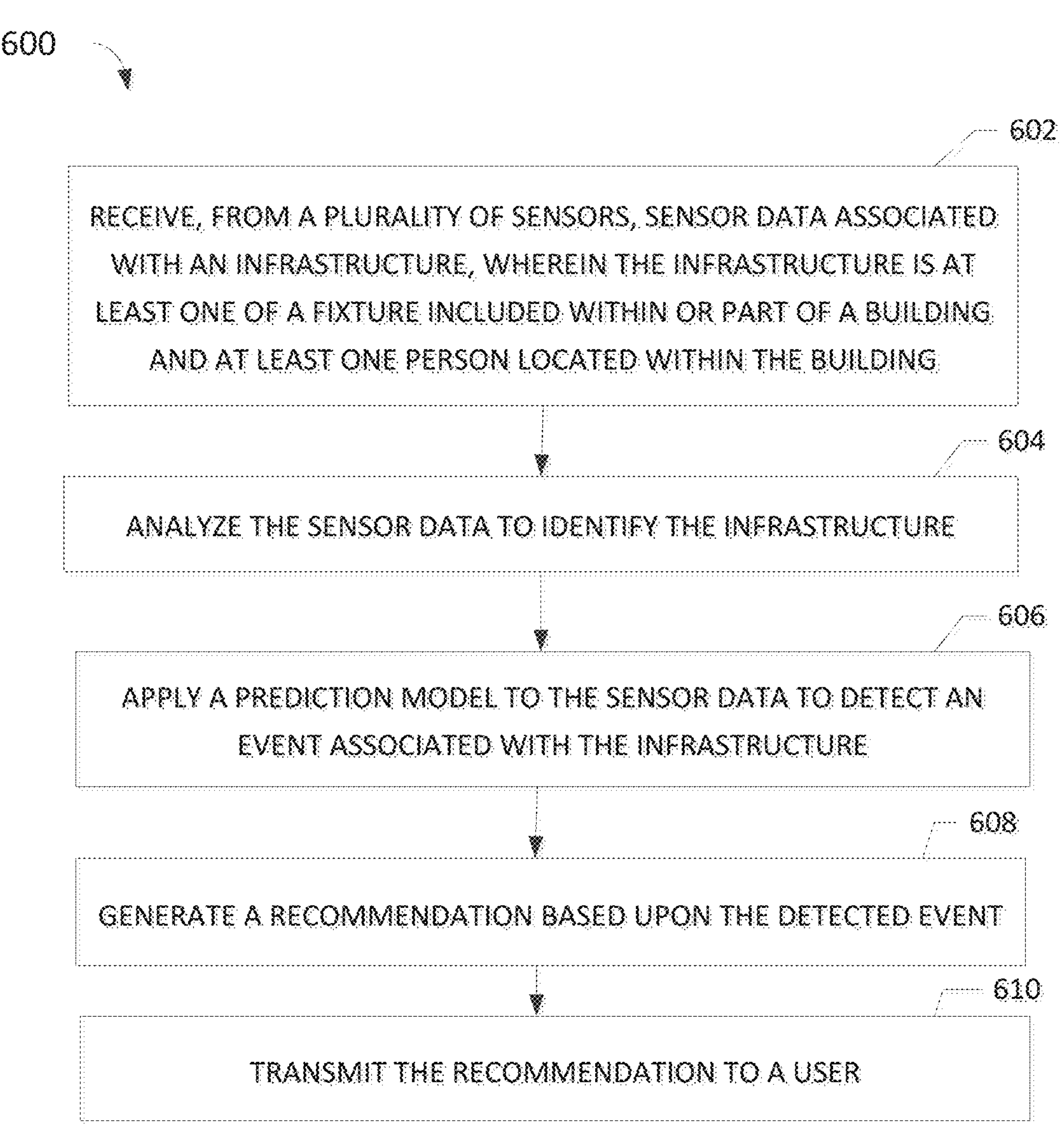
FIG. 6 illustrates a flow chart of an exemplary computer-implemented process for generating a recommendation, in accordance with one embodiment of the present disclosure.

FIG. 6 illustrates a flow chart of an exemplary computer-implemented process 600 for generating a recommendation. In the exemplary embodiment, the computer-implemented method illustrated in flow chart 600 is implemented by a computing device such as BA server 108 (shown in FIG. 1). Recommendation module 426 (shown in FIG. 4) of BA server 108 may be used to generate recommendations. In the exemplary embodiment, BA server 108 may be in communication with a hub 110 (shown in FIG. 1) and a user computing device associated with a building owner (e.g., homeowner 106, shown in FIG. 1), such as user computing device 402 (shown in FIG. 4).

In the exemplary embodiment, BA server 108 receives 602 sensor data associated with an infrastructure from a plurality of sensors, such as sensors 112 (shown in FIG. 1). The infrastructure is at least one of (i) a fixture included within or part of the building and (ii) person(s) located in the building. BA server 108 may receive sensor data from hub 110 for a building, such as building 104 (shown in FIG. 1). BA server 108 further analyzes 604 the received sensor data to identify at least one infrastructure. BA server 108 applies 606 a prediction model to the received sensor data to detect an event associated with the infrastructure. The prediction model may utilize artificial intelligence algorithms to detect events and identify correlations between events to detect building trends. The prediction model may be configured to compare received sensor data to reference parameters.

BA server 108 further generates 608 a recommendation based upon the detected event. In the example embodiment, BA server 108 utilizes recommendation module 426 (shown in FIG. 4) to recommend a course of action for homeowner 106. The course of action may be a preventive action to prevent breakdowns and failures of fixtures, electronic devices, and structural systems of building 104. The course of action may be a corrective action to address building failures and compromises. In the exemplary embodiment, BA server 108 transmits 610 the recommendation to a user, such as homeowner 106. BA server 108 may transmit the recommendation to a registered user computing device, such as user computing device 402, to alert the homeowner 106 of the detected event.

In some embodiments, BA server 108 also transmits an analysis of the detected event and/or trend to homeowner 106 to enable homeowner 106 to review the analyzed sensor data and confirm or deny the detected event and/or identified trends. In other embodiments, BA server 108 may provide homeowner 106 with an option to accept or deny the recommended course of action. BA server 108 may save the responses from homeowner 106 in memory 406 (shown in FIG. 4). In some embodiments, BA server 108 may enable homeowner 106 to refute (e.g., question) the detected event and/or identified trends. In these embodiments, BA server 108 may be configured to flag the refuted event and/or trend for further evaluation.

Exemplary Computer-Implemented Method for Automatically Deploying a Response Device FIG. 7 illustrates a flow chart 700 of an exemplary computer-implemented process 700 for automatically deploying a response device to address a detected event. In the exemplary embodiment, the computer-implemented method illustrated in flow chart 700 is implemented by a computing device such as BA server 108 (shown in FIG. 1). In the exemplary embodiment, BA server 108 may be in communication with a hub, such as hub 110 (shown in FIG. 1), and a user computing device associated with a building owner (e.g., homeowner 106, shown in FIG. 1), such as user computing device 402 (shown in FIG. 4).

In the exemplary embodiment, BA server 108 receives 702 sensor data from a plurality of sensors, such as sensors 112 (shown in FIG. 1). BA server 108 may receive sensor data from 110 for a building, such as building 104 (shown in FIG. 1). BA server 108 further analyzes 704 the received sensor data to identify at least one infrastructure. For example, BA server 108 may detect that sensor data has been collected for kitchen 208 (shown in FIG. 2), and more specifically, for appliances, such as refrigerator 212 (shown in FIG. 2), as well as the air quality of the kitchen. BA server

108 applies 706 a prediction model, to the received sensor data to detect an event associated with the infrastructure. The prediction model may utilize artificial intelligence algorithms to detect events and identify correlations between events to detect trends. The prediction model may be configured to compare received sensor data to reference parameters.

In the exemplary embodiment, BA server 108 automatically deploys 708 a response device to address the detected event. The response device may be a portable sensing device, such as portable sensing device 210 (shown in FIG. 2). In some embodiments, the response device may be a robotic arm, or other type of robot, such as a robotic rover with one or more robotic arms or sensors (including cameras), or an aerial robot or drone with various sensors or cameras. In the exemplary embodiment, the response device is configured to take corrective action on behalf of homeowner 106. For example, BA server 108 may detect that homeowner 106 left refrigerator 212 door open before leaving building 104. In this example, BA server 108 may instruct the response device to take corrective action on behalf of homeowner 106, and to close refrigerator 212 door.

In further embodiments, BA server 108 may detect an event, and instruct the response device to collect additional data regarding the detected event. For example, BA server 108 may detect, from sensor data, the presence of nitrogen dioxide and/or carbon monoxide in kitchen 208. However, BA server 108 may not detect the presence of a flame on the gas burner of the stove. In this example, BA server 108 may instruct the response device to travel to kitchen 208 and take photos or otherwise collect imaging data of the kitchen to identify where the source of the detected pollutants.

Exemplary Computer-Implemented Method for Generating a Savings Plan to Finance Future Building Repairs FIG. 8 illustrates a flow chart of an exemplary computer-implemented process 800 for generating a savings plan to finance future building repairs. In the exemplary embodiment, the computer-implemented method illustrated in flow chart 800 is implemented by a computing device such as BA server 108 (shown in FIG. 1). In the exemplary embodiment, BA server 108 may be in communication with a hub, such as hub 110 (shown in FIG. 1) and a user computing device associated with a building owner (e.g., homeowner 106, shown in FIG. 1), such as user computing device 402 (shown in FIG. 4). In some embodiments, BA server 108 may be in communication with a financial institution (not shown) associated with homeowner 106.

In the exemplary embodiment, BA server 108 receives 802 sensor data from a plurality of sensors, such as sensors 112 (shown in FIG. 1) related to at least one infrastructure. BA server 108 may receive sensor data from hub 110. BA server 108 may receive baseline data during an enrollment (e.g., registration) process. During the registration process, BA server 108 may collect baseline data, such as initial sample data of the at least one infrastructure to be monitored by BA server 108.

In the exemplary embodiment, BA server 108 generates 804 an infrastructure profile for the infrastructure. The infrastructure profile includes sensor data associated with the infrastructure. The infrastructure profile may include baseline data collected during the enrollment process. In further embodiments, the infrastructure profile may be updated to include data samples received from sensors over a period of time. Over time, the infrastructure profile may include historical sensor data associated with different periods of time as well as new data samples associated with an infrastructure.

In the exemplary embodiment, BA server 108 compares 806 the sensor data to an optimal profile for the infrastructure. The optimal profile includes at least one reference parameter representative of an optimal condition for the monitored infrastructure. BA server 108 further determines 808, based upon the comparison, a condition of the infrastructure. For example, BA server 108 may compare baseline data for an infrastructure, such as a sump pump, with an optimal profile including optimal operating parameters for known sump pumps of the same model. Based upon the comparison, BA server 108 may determine that the sump pump in building 104 is pumping at peak efficiency.

In the exemplary embodiment, BA server 108 applies 810 an artificial intelligence model to the received sensor data to generate a maintenance timeline for the infrastructure being monitored. The model may utilize reference data, such as utility meter readings, as well as historic sensor data to determine patterns of usage. BA server 108 may predict, based upon patterns of usage and the initial condition of the infrastructure, when a specific infrastructure will need to be repaired or replaced. BA server 108 further calculates 812 an estimated cost of repair for the at least one infrastructure being monitored based upon the maintenance timeline. BA server 108 may determine an estimated cost of replacing or repairing the infrastructure.

For example, BA server 108 may detect that a sump pump in building 104 is nine years old. BA server 108 may detect that the sump pump is operating at acceptable conditions. BA server 108 may build an optimal profile for the sump pump by retrieving operating parameters for a sump pump of the same model and make from memory 406 or from reference parameters database 418 (both shown in FIG. 4). BA server 108 may compare the infrastructure profile for the sump pump to the optimal profile to determine that the average life span for the sump pump in building 104 is 10 years. Accordingly, BA server 108 may estimate that, given the current condition of the sump pump, the sump pump should be replaced within the next year. BA server 108 may retrieve, from memory 406 or reference parameters database 418, prices for a replacement sump pump of similar model and make as well as installation costs associated with technicians in the area to calculate 812 an estimated cost of repair.

In the exemplary embodiment, BA server 108 generates 814 a savings plan based upon the generated maintenance timeline and the estimated cost of repair. The savings plan may recommend opening a savings account (e.g., building maintenance savings account) to finance future home repairs. BA server 108 may recommend designating a specific percentage or dollar amount of homeowner's 106 monthly paycheck into the savings account to fund future home repairs and maintenance projects. The recommended percentage or dollar amount may be based upon how costly the estimated cost of repair is, as well as the projected timeline for repairing the given infrastructure.

In the exemplary embodiment, BA server 108 transmits 816 a message to the user (e.g., homeowner 106) to enroll in the savings plan. The savings plan may be for one or more infrastructures being monitored by BA server 108. In another embodiment, the savings plan may take into consideration maintenance timelines and projected costs for a plurality of infrastructures being monitored for building 104. In some embodiments, BA server 108 may receive financial data from homeowner 106 and/or from a financial institution associated with homeowner 106. In these embodiments, BA server 108 may take the homeowner's 106 financial information into consideration when calculating how much money should be set aside for future home repairs. In other embodiments, homeowner 106 may provide BA server 108 with a payment account identifier, and authorize BA server 108 to link a payment account associated with homeowner to a savings account (e.g., savings fund) maintained by BA server 108.

In further embodiments, BA server 108 may receive a user response to the recommendation to enroll in a savings plan. For example, based upon the maintenance timeline and estimated costs of repair, homeowner 106 may indicate that he or she would like to set aside a specific amount from his or her paycheck each month for a designated period of time. In this example, homeowner 106 may authorize his or her financial institution to automatically deposit the designated amount each month in a savings fund maintained by BA server 108.

In some embodiments, BA server 108 may be configured to create an inventory of all the infrastructures of building 104 registered for monitoring by BA server 108. The inventory may include baseline data as to an initial condition of each infrastructure. Accordingly, BA server 108 may compare subsequent sensor data to the baseline data to detect changes to an infrastructure's condition (e.g., deterioration, wear and tear) over time.

Figure 9:
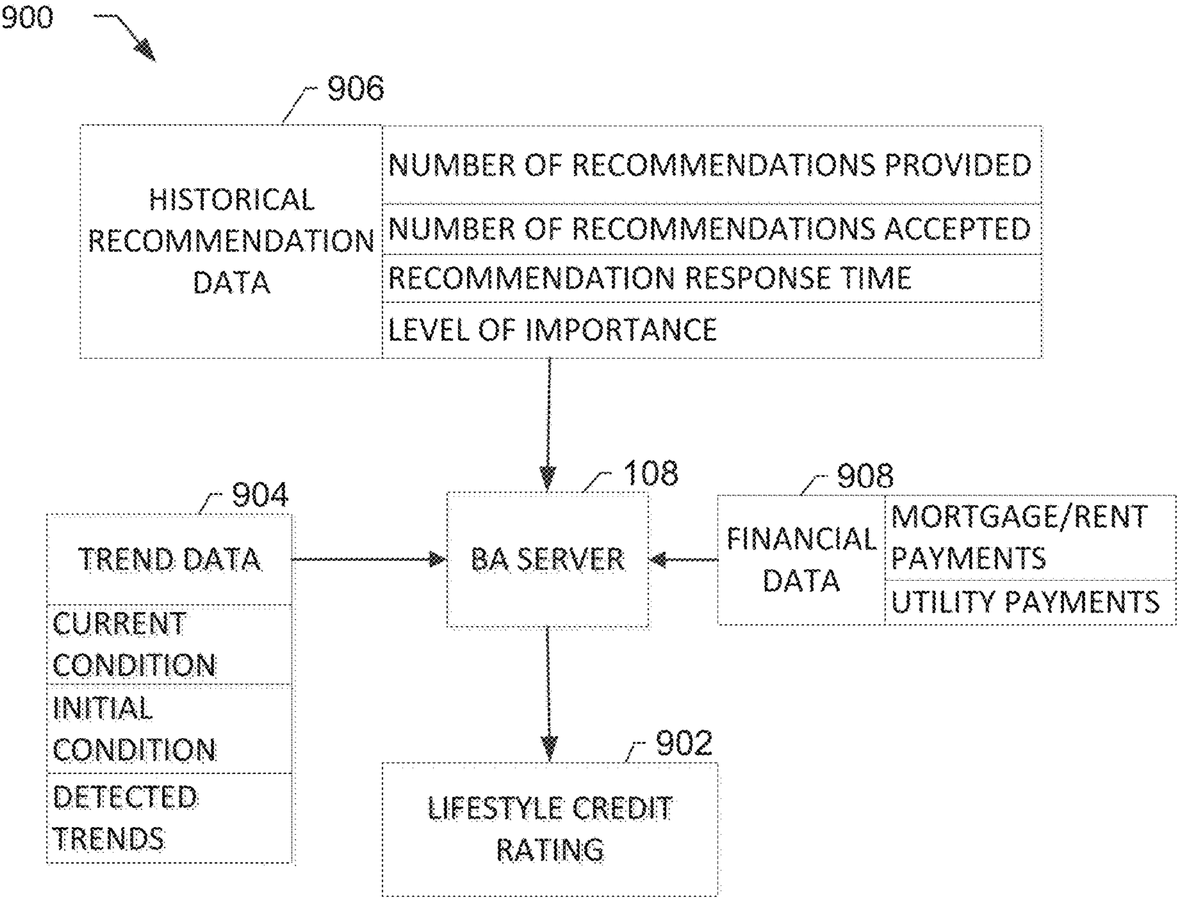
FIG. 9 illustrates a simplified block diagram of an exemplary process for generating a lifestyle credit rating for a building owner, in accordance with one aspect of the present disclosure.

Exemplary Data Conversion Process for Generating a Lifestyle Credit Rating for a Building Owner FIG. 9 is a simplified block diagram 900 of an exemplary process using BA server 108 for generating a lifestyle credit rating 902 for a building owner, such as homeowner 106 (both shown in FIG. 1). In the exemplary embodiment, diagram 900 includes BA server 108, trend data 904, historical recommendation data 906, and financial data 908.

In the exemplary embodiment, trend data 904 includes sensor data, such as sensor data 502 (shown in FIG. 5), that has been analyzed to detect building events and trends. Trend data 904 may include data as to an initial condition of an infrastructure, a current condition of an infrastructure, and detected trends for a given infrastructure. For example, BA server 108 may detect a problem with the wiring system of building 104 by detecting that outlets in multiple rooms of building 104 are not operating. BA server 108 may also detect that outlets in the garage or on exterior walls of building 104 are also not working. BA server 108 may determine that there is a correlation between these detected events, and predict that there is problem with the wiring system of building 104 rather than an isolated problem with one faulty outlet.

In the exemplary embodiment, historical recommendation data 906 includes records of recommendations generated by BA server 108 and provided to homeowner 106. These records may include a total number of recommendations provided to homeowner 106, the total number of recommendations accepted (e.g., followed) by homeowner 106, a level of importance (e.g., priority) for each recommendation, a response time associated with each recommendation, and reasons provided by homeowner 106 for accepting or ignoring certain recommendations. In some embodiments, recommendations provided to homeowner 106 may indicate a level of priority, such as urgent priority (e.g., roof leak, foundation leak, burning insulation), high priority (e.g., leaky valves, degrading window seals), medium priority (e.g., dusty fan grates), and low priority (e.g., burnt light bulbs). In other embodiments, recommendations provided to homeowner 106 may indicate whether each recommendation is for a preventative action or a corrective action to be taken by homeowner 106.

In the exemplary embodiment, financial data 908 may include data representative of payment behavior. Financial data 908 may include records of mortgage or rent payments made by homeowner 106 for building 104, as well as records of past utility payments made for building 104. BA server 108 may assess, from financial data 908, whether homeowner 106 displays a pattern of making late or timely building payments (e.g., mortgage/rent payments, utility payments, insurance payments) each month.

In the exemplary embodiment, BA server 108 uses the above-described datasets in evaluating homeowner's 106 behavior with respect to maintaining building 104 to generate a lifestyle credit rating 902 for homeowner 106. BA server 108 may utilize one or more of the above-described data sets to generate lifestyle credit rating 902. Lifestyle credit rating 902 may be an assessment of homeowner's 106 behavior with regards to building maintenance and care. In one example, BA server 108 may evaluate the number of recommendations followed by homeowner 106, and determine that homeowner 106 is very responsive to the recommendations provided by BA server 108. In the same example, BA server 108 may detect that the overall condition of building 104 has steadily improved due to a number of urgent and/or high priority recommendations followed by homeowner 106.

BA server 108 may be in communication with computing devices of insurer network 410 (shown in FIG. 4). In the exemplary embodiment, lifestyle credit rating 902 may be used to offer different types of incentives to homeowner 106, such as quotes for life insurance and/or automobile insurance policies. BA server 108 may determine that, based upon a high lifestyle credit rating 902, homeowner 106 demonstrates responsible behavior as a property owner or property renter. In some embodiments, BA server 108 may adjust premiums for homeowner 106 based upon a number of preventative actions taken by homeowner 106.

Users associated with each property (such as property 304, shown in FIG. 3) may opt-in for one or more of the above-described monitoring services provided by BA server 108. Properties registered for monitoring by BA server 108 may include multi-building and/or multi-residential properties (e.g., apartments, condominiums). In some embodiments, a user may be a landlord of one or more properties, a property manager who manages multiple properties, and/or a third party associated with a property (e.g., a utility company). In these embodiments, all of the monitoring services available to a homeowner may not be available to these users. For example, a property manager user registering an apartment complex for monitoring by BA server 108 may not opt in to receive lifestyle credit ratings or to enroll in a maintenance savings account. In other embodiments, monitoring services specific to homeowner users may not be available to landlord and/or property manager users. In these embodiments, these users may register for monitoring services provided by BA server 108 that enable residents, a landlord, and/or a building maintenance team to be preemptively notified of corrective actions that can be taken to minimize exposure to building damage, and to protect the health and safety of building occupants.

Exemplary Building Analysis (BA) Server

Figure 10:
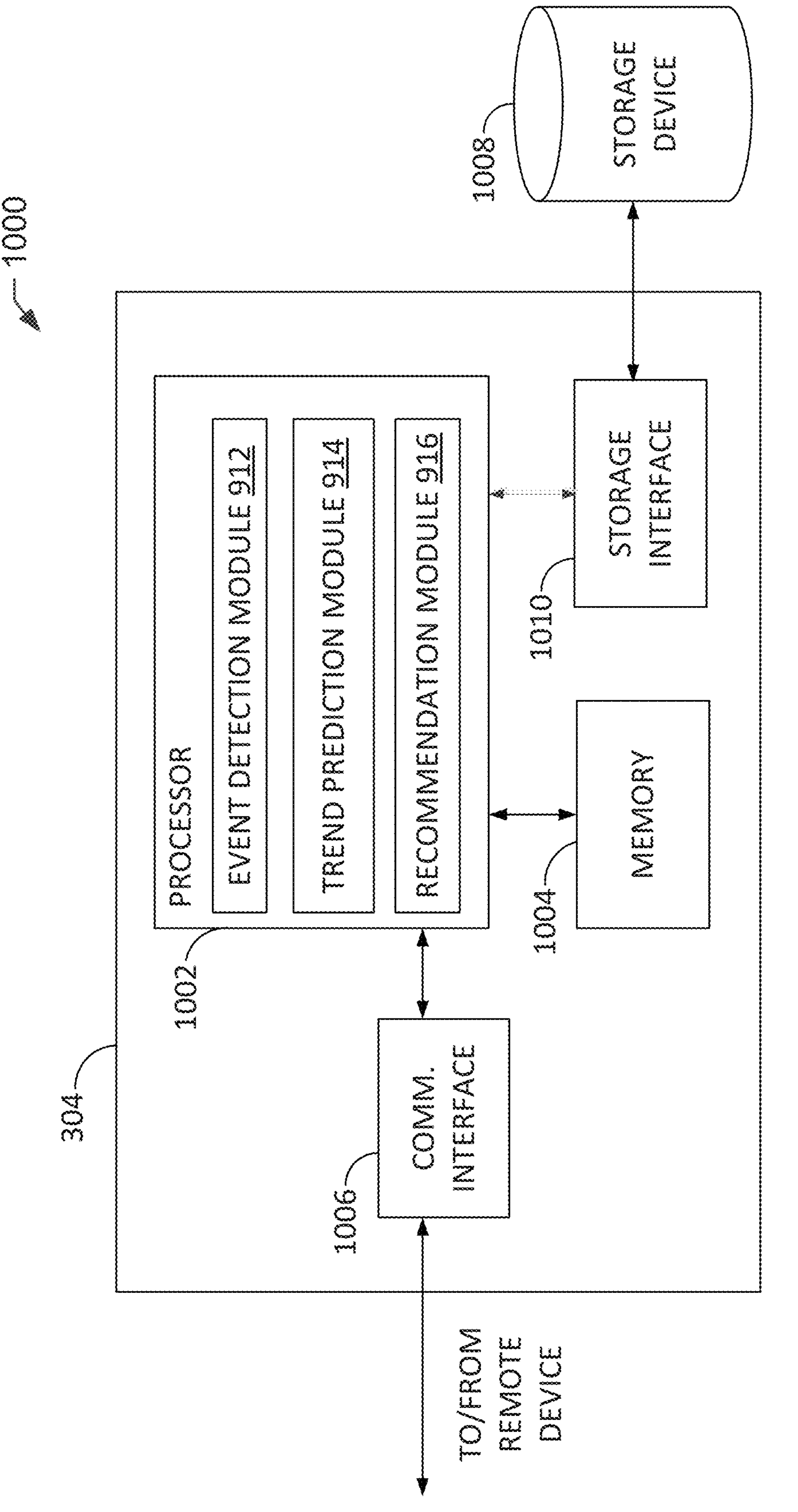
FIG. 10 illustrates an exemplary configuration of the building analysis (BA) server (shown in FIG. 1), in accordance with one embodiment of the present disclosure.

FIG. 10 depicts an exemplary configuration 1000 of building analysis (BA) server 108 (shown in FIG. 1) in accordance with one embodiment of the present disclosure. BA server 108 includes a processor 1002 for executing instructions. Instructions are stored in a memory area 1004, for example. Processor 1002 includes one or more processing units. The one or more processing units may be in a multi-core configuration.

In the exemplary embodiment, processor 1002 is operable to execute event detection module 422, trend prediction module 424, and recommendation module 426. Modules 422, 424, and 426 may include specialized instruction sets, and/or coprocessors. Event detection module 422 may detect an event associated with a building, such as building 104 (shown in FIG. 1). Detected events may include the presence of gas and/or pollutants, open windows, electronic appliances and equipment e.g., air conditioning and heat pump devices) being turned on and off or otherwise being used by an occupant, such as homeowner 106 (shown in FIG. 1). Trend prediction module 424 may detect correlations between events to predict trends (e.g., patterns) associated with monitored infrastructures of building 104.

Recommendation module 426 may be configured to generate recommendations to homeowner 106 based upon detected events and trends of monitored infrastructures. For example, recommendation module 426 may recommend corrective and/or preventative actions to homeowner 106. Recommendation module 426 may recommend that homeowner 106 enroll in a savings plan to finance future home repairs and maintenance projects. Recommendation module 426 may further be configured to recommend homeowner 106 to seek medical attention based upon sensor data indicative of a medical condition and/or symptom. Recommendations may be configurable. In some embodiments, recommendation module 426 may be configured to generate recommendations for recommendation categories and/or types that homeowner 106 has specifically opted-in for.

In further embodiments, processor 1002 may be configured to build prediction models based upon training data (e.g., test data) and historic sensor data, which may all be stored in memory area 1004. Models may be utilized to recognize registered infrastructures, detect building events, and predict trends.

In the exemplary embodiment, processor 1002 is operatively coupled to a communication interface 1006 such that BA server 108 is capable of communicating with remote device(s) such as hubs 110, user computing devices 402, insurer network 410, and utility company network 412 (all shown in FIG. 4). For example, communication interface 1006 may receive requests for recommendation records from computer devices associated with, for example, insurer network 410 and/or utility company network 412 via the Internet or other network.

Processor 1002 may also be operatively coupled to a storage device 1008. Storage device 1008 may be any computer-operated hardware suitable for storing and/or retrieving data. In some embodiments, storage device 1008 may be integrated in BA server 108. For example, BA server 108 may include one or more hard disk drives as storage device 1008. In other embodiments, storage device 1008 is external to BA server 108 and is accessed by a plurality of computer devices. For example, storage device 1008 may include a storage area network (SAN), a network attached storage (NAS) system, a cloud based storage system, and/or multiple storage units such as hard disks and/or solid state disks in a redundant array of inexpensive disks (RAID) configuration.

In some embodiments, processor 1002 may be operatively coupled to storage device 1008 via a storage interface 1010. Storage interface 1010 may be any component capable of providing processor 1002 with access to storage device 1008. Storage interface 1010 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1002 with access to storage device 1008.

Processor 1002 may execute computer-executable instructions for implementing aspects of the disclosure. In some embodiments, processor 1002 may be transformed into a special purpose microprocessor by executing computer-executable instructions or by otherwise being programmed. For example, processor 1002 may be programmed with the instruction such as those illustrated in FIGS. 6, 7, and 8.

Memory areas 1004 and 406 (shown in FIG. 4) may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

Exemplary Client Computing Device

Figure 11:
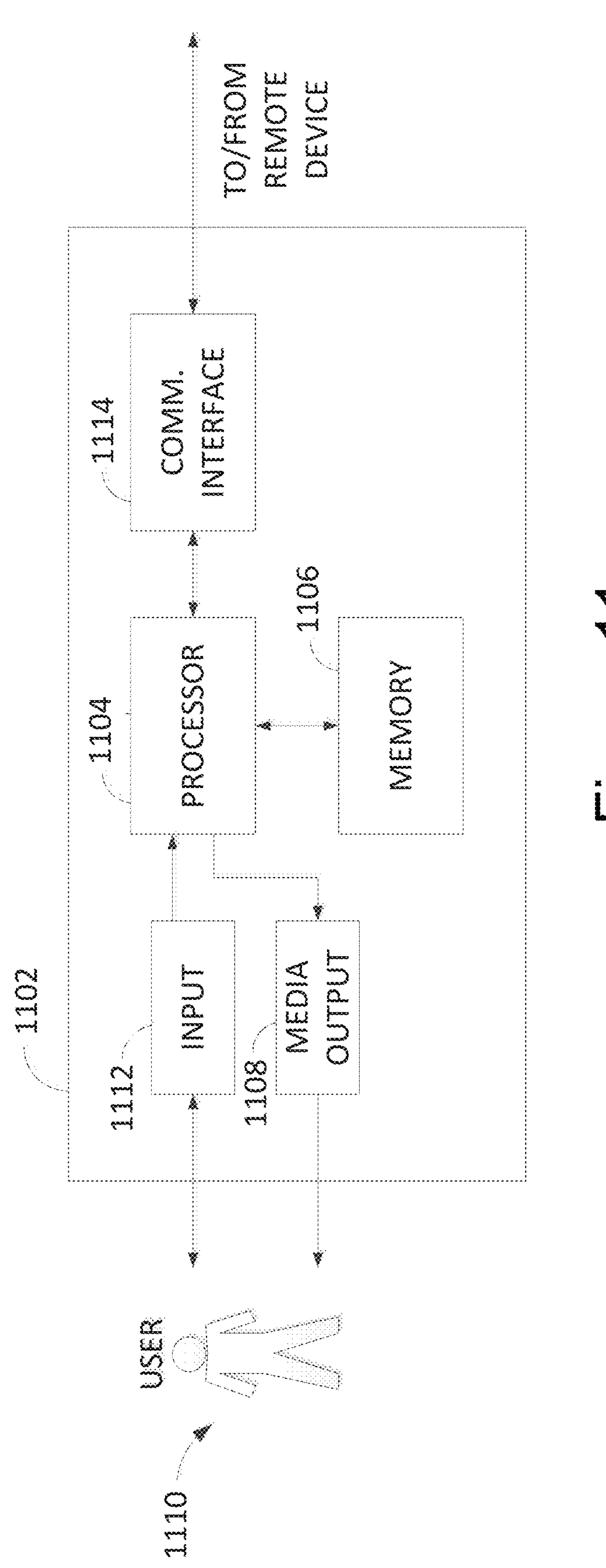
FIG. 11 illustrates an exemplary configuration of a client computing device, in accordance with one embodiment of the present disclosure.

FIG. 11 illustrates an exemplary configuration 1100 of a client computing device 1102. Client computing device 1102 may be, for example, at least one of user computing device 402 and hub 110 (both shown in FIG. 4).

Client computing device 1102 may include a processor 1104 for executing instructions. In some embodiments, executable instructions may be stored in a memory area 1106. Processor 1104 may include one or more processing units (e.g., in a multi-core configuration). Memory area 1106 may be any device allowing information such as executable instructions and/or other data to be stored and retrieved. Memory area 1106 may include one or more computer readable media.

In exemplary embodiments, client computing device 1102 may also include at least one media output component 1108 for presenting information to a user 1110, such as homeowner 106 (shown in FIG. 1). Media output component 1108 may be any component capable of conveying information to user 1110. In some embodiments, media output component 1108 may include an output adapter such as a video adapter and/or an audio adapter. An output adapter may be operatively coupled to processor 1104 and operatively couplable to an output device such as a display device (e.g., a liquid crystal display (LCD), light emitting diode (LED) display, organic light emitting diode (OLED) display, cathode ray tube (CRT) display, "electronic ink" display, or a projected display) or an audio output device (e.g., a speaker or headphones).

Client computing device 1102 may also include an input device 1112 for receiving input from user 1110. Input device 1112 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen may function as both an output device of media output component 1108 and input device 1112.

Client computing device 1102 may also include a communication interface 1114, which can be communicatively coupled to a remote device, such as BA server 108 or hub 110. Communication interface 1114 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 1106 may be, for example, computer readable instructions for providing a user interface to user 1110 via media output component 1108 and, optionally, receiving and processing input from input device 1112. A user interface may include, among other possibilities, a web browser and client application. Web browsers may enable users, such as user 1110, to display and interact with media and other information typically embedded on a web page or a website. A client application may allow user 1110 to interact with a server application from BA server 108.

Memory area 1106 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are exemplary only, and are thus not limiting as to the types of memory usable for storage of a computer program.

Exemplary Embodiments & Functionality

In one aspect, a building analysis ("BA") system for detecting events of a building may be provided. The BA system may include a plurality of sensors positioned within a building. The plurality of sensors may be configured to detect a condition associated with an infrastructure of the building. The infrastructure may be at least one of (i) a fixture associated with the building and (ii) at least one person located within the building. The BA system may also include a memory device including an optimal profile of the infrastructure. The optimal profile may include characteristics representative of an optimal condition for the infrastructure. The BA system may also include a building analysis ("BA") server communicatively coupled to the plurality of sensors. The BA server may include one or more processors in communication with the memory device.

The one or more processors may be programmed to: (i) receive, from the plurality of sensors, sensor data related to the infrastructure, (ii) compare the received sensor data to the optimal profile to detect an event associated with the infrastructure, (iii) generate, based upon the comparison, an alert message that includes the detected event and a recommended action for an owner of the building, wherein the recommended action is at least one of a preventative action or a corrective action, and/or (iv) transmit the alert message to a user computing device associated with the owner of the building. The BA computer system may include additional, less, or alternate functionality, including those discussed elsewhere herein.

For instance, the one or more processors may be programmed to direct or take one or more preventative or corrective actions, including those discussed elsewhere herein.

An additional enhancement may be where comparing the received sensor data to the optimal profile to detect the event associated with the infrastructure includes determining a difference between the received sensor data and the optimal condition within the optimal profile. Another enhancement may be where the one or more processors are configured to generate an infrastructure profile for the infrastructure. The infrastructure profile may include sensor data received over a period of time.

Another enhancement may be where the fixture is at least one of an electronic device within the building, a utility equipment, and a construction material of the building. A further enhancement may be where the plurality of sensors include at least one a camera, microphone, air particle sensor, light sensor, and accelerometer. Another enhancement may be where the detected event is an environmental condition within the building, the environmental condition being a presence of at least one of carbon dioxide, carbon monoxide, smoke, and allergens.

A further enhancement may be where the optimal profile includes optimal maintenance parameters for the fixture. The one or more processors may be programmed to: (i) receive, from the plurality of sensors, over a baseline period of time, sample data as to a condition of the fixture, (ii) generate, based upon the sample data and the optimal maintenance parameters, a prediction model associated with the fixture, and/or (iii) determine when the fixture needs to be at least one of repaired and replaced by applying the prediction model to the received sensor data.

A further enhancement may be where the recommended action is at least one of repairing and replacing the fixture within a designated period of time. A further enhancement may be where the alert message includes an estimated cost and third-party contact information for performing the recommended action. Another enhancement may be here the alert message notifies the owner as to a potential health hazard due to a current condition of the fixture.

Another enhancement may be where the one or more processors are further programmed to: (i) receive, from the user computing device, a user input accepting or denying the recommended action and/or (ii) store the user input to the recommended action in the memory device.

Another enhancement may be where the one or more processors are further programmed to: (i) generate a historic record of recommended actions provided to the building owner, where the historic record indicates which of the recommended actions was accepted and denied by the owner, (ii) determine, from the historical record, a lifestyle credit rating for the owner, where the lifestyle credit rating is a building owner behavior assessment based upon a number of recommended actions accepted by the building owner, and/or (iii) transmit, based upon the lifestyle credit rating, to the user computing device, an offer for at least one of an automobile insurance policy and a life insurance policy to the building owner.

Another enhancement may be where the one or more processors are further programmed to transmit the sensor data to a remote-computing device to update an insurance policy associated with the owner of the building. A further enhancement may be where the fixture is a utility equipment. The one or more processors may be further programmed to transmit the sensor data to a third-party computing device to detect a utility failure associated with a plurality of buildings.

Another enhancement may be where the alert message includes an estimated cost and projected timeline associated with repairing the fixture. The recommended action may be creating a building maintenance savings account to budget costs associated with repairing the fixture.

Another enhancement may be where the one or more processors are further programmed to: (i) transmit, to a user computing device associated with the owner, a request to create a building maintenance savings account to repair the fixture, (ii) receive, from the owner, approval to create the building maintenance savings account and a payment account identifier associated with a payment account of the owner, (iii) link the building maintenance savings account with the payment account, and/or (iv) automatically deposit, from the payment account into the savings account, a designated amount for a predetermined period of time until an amount substantially equal to the estimated cost is within the building maintenance savings account.

A further enhancement may be where the plurality of sensors are configured to detect audio data associated with the at least one person located within the building. The optimal profile may include an audio sample associated with the at least one person. The one or more processors may be further configured to: (i) receive, from the plurality of sensors, audio data associated with the at least one person, (ii) compare the audio data to the optimal profile to detect a health event associated with the at least one person, and/or (iii) generate, based upon the analysis, a health alert message for the owner of the building.

A further enhancement may be where the plurality of sensors are configured to differentiate between audio data associated with the fixture and the at least one person. Another enhancement may be where the health event is at least one of a coughing sound and a sneezing sound. Another enhancement may be where the one or more processors are further configured to determine that the audio data is associated with the owner.

A further enhancement may be where the memory device includes historical audio data associated with the at least one person. The one or more processors may be further configured to: (i) compare the audio data to the historical audio data to detect a trend, (ii) determine a correlation between the detected trend and a potential health condition, and/or (iii) generate a health alert message to alert the owner of the potential health condition.

In a further aspect, at least one non-transitory computer-readable storage media having computer-executable instructions embodied thereon may be provided. When executed by a building analysis ("BA") server communicatively coupled to a plurality of sensors positioned within a building, the plurality of sensors may be configured to detect a condition associated with an infrastructure of the building. The infrastructure may be at least one of (i) a fixture associated with the building, and (ii) at least one person located within the building. The BA server may include one or more processors in communication with the memory device. The memory device may include an optimal profile of the infrastructure. The optimal profile may include characteristics representative of an optimal condition for the infrastructure.

The computer-executable instructions may cause the one or more processors to: (i) receive, from the plurality of sensors, sensor data related to the infrastructure, (ii) compare the received sensor data to the optimal profile to detect an event associated with the infrastructure, (iii) generate, based upon the comparison, an alert message that includes the detected event and a recommended action for an owner of the building, wherein the recommended action is at least one of a preventative action or a corrective action, and/or (iv) transmit the alert message to a user computing device associated with the owner of the building. The computer-executable instructions may include additional, less, or alternate functionality, including those discussed elsewhere herein.

In another aspect, a building analysis ("BA") system for detecting events of a building may include (1) a plurality of sensors positioned within a building, the plurality of sensors being configured to detect a condition associated with an infrastructure of the building, wherein the infrastructure is at least one of (i) a fixture associated with the building, and (ii) at least one person located within the building; (2) a memory device including an optimal profile of the infrastructure, the optimal profile including characteristics representative of an optimal condition for the infrastructure; and/or (3) a building analysis ("BA") server communicatively coupled to the plurality of sensors, the BA server including one or more processors in communication with the memory device, wherein the one or more processors are programmed to: (a) receive, from the plurality of sensors, sensor data related to the infrastructure; (b) compare the received sensor data to the optimal profile to detect an event associated with the infrastructure; (c) determine a recommended action based upon the detected event, wherein the recommended action is at least one of a preventative action or a corrective action; and/or (d) execute (e.g., carry out, direct, or take) the recommended action to mitigate at least one of damage caused by the detected event to the building and injury caused by the detected event to the at least one person associated with the building. The BA system may include additional, less, or alternate functionality, including that discussed elsewhere herein.

For instance, the one or more processors may be configured to (i) generate an alert message detailing the detected event and the recommended action, and (ii) transmit the alert message to a mobile device or other user computing device associated with a building owner (e.g., owner of the building). In some embodiments, the recommended action is taken after receiving building owner approval via an electronic message sent from their mobile device or other user computing device.

A further embodiment may be where the one or more processors are configured to compare the received sensor data to the optimal profile to detect the event associated with the infrastructure by determining a difference between the received sensor data and the optimal condition within the optimal profile. A further embodiment may be where the one or more processors are configured to generate an infrastructure profile for the infrastructure, wherein the infrastructure profile includes sensor data received over a period of time.

An additional embodiment may be where the fixture is at least one of an electronic device within the building, a utility equipment, and a construction material of the building. Another embodiment may be where the plurality of sensors include at least one a camera, microphone, air particle sensor, light sensor, and accelerometer. A further embodiment may be where the detected event is an environmental condition within the building. The environmental condition may be a presence of at least one of carbon dioxide, carbon monoxide, smoke, and allergens.

A further embodiment may be where the optimal profile includes optimal maintenance parameters for the fixture. The one or more processors may be programmed to (i) receive, from the plurality of sensors, over a baseline period of time, sample data as to a condition of the fixture, (ii) generate, based upon the sample data and the optimal maintenance parameters, a prediction model associated with the fixture, and/or (iii) determine, by applying the prediction model to the received sensor data, when the fixture needs to be at least one of repaired and replaced.

An additional embodiment may be where the recommended action is at least one of repairing and replacing the fixture within a designated period of time. Another embodiment may be where the alert message includes an estimated cost and third-party contact information for performing the recommended action. A further embodiment may be where the alert message notifies the owner as to a potential health hazard due to a current condition of the fixture.

A further embodiment may be where the one or more processors are further programmed to (i) receive, from the user computing device, a user input accepting or denying the recommended action and/or (ii) store the user input for the recommended action in the memory device.

A further embodiment may be where the one or more processors are further programmed to (i) generate a historic record of recommended actions provided to an owner, wherein the historic record indicates which of the recommended actions was accepted and denied by the owner, (ii) determine, from the historical record, a lifestyle credit rating for the owner of the building, wherein the lifestyle credit rating is a building owner behavior assessment based upon a number of recommended actions accepted by the building owner, and/or (iii) transmit, based upon the lifestyle credit rating, to a user computing device associated with the owner, an offer for at least one of an automobile insurance policy and a life insurance policy to the owner.

An additional embodiment may be where the one or more processors are further programmed to transmit the sensor data to a remote computing device to update an insurance policy associated with a building owner of the building. Another embodiment may be where the fixture is a utility equipment. The one or more processors may be further programmed to transmit the sensor data to a third-party computing device to detect a utility failure associated with a plurality of buildings.

A further embodiment may be where the one or more processors are further programmed to (i) transmit, to a user computing device associated with the owner, a request to create a building maintenance savings account to repair the fixture, (ii) receive, from the owner, approval to create the building maintenance savings account and a payment account identifier associated with a payment account of the owner, (iii) link the building maintenance savings account with the payment account, and/or (iv) automatically deposit, from the payment account into the savings account, a designated amount for a predetermined period of time until an amount substantially equal to the estimated cost is within the building maintenance savings account.

A further embodiment may be where the plurality of sensors are configured to detect audio data associated with the at least one person located within the building. The optimal profile may include an audio sample associated with the at least one person. The one or more processors may be further configured to (i) receive, from the plurality of sensors, audio data associated with the at least one person, (ii) compare the audio data to the optimal profile to detect a health event associated with the at least one person, and/or (iii) generate, based upon the analysis, a health alert message for an owner of the building.

A further embodiment may be where the plurality of sensors are configured to differentiate between audio data associated with the fixture and the at least one person. A further embodiment may be where the health event is at least one of a coughing sound and a sneezing sound. Another embodiment may be where the one or more processors are further configured to determine that the audio data is associated with the owner.

A further embodiment may be where the memory device includes historical audio data associated with the at least one person. The one or more processors may be further configured to (i) compare the audio data to the historical audio data to detect a trend, (ii) determine a correlation between the detected trend and a potential health condition, and/or (iii) generate the health alert message to alert the owner of the potential health condition.

In another aspect, a computer-implemented method for detecting events of a building may be provided that is implemented using a building analysis ("BA") system. The BA system may include (a) a plurality of sensors positioned within a building, the plurality of sensors configured to detect a condition associated with an infrastructure of the building, wherein the infrastructure is at least one of (i) a fixture associated with the building and (ii) at least one person located within the building, (b) a memory device including an optimal profile of the infrastructure, the optimal profile including characteristics representative of an optimal condition for the infrastructure, and (c) a building analysis ("BA") server communicatively coupled to the plurality of sensors. The BA server may include one or more processors in communication with the memory device. The method may include (1) receiving, from the plurality of sensors, sensor data related to the infrastructure; (2) comparing the received sensor data to the optimal profile to detect an event associated with the infrastructure; (3) determining a recommended action based upon the detected event, wherein the recommended action is at least one of a preventative action or a corrective action; and/or (4) executing (e.g., carrying out, directing, or taking) the recommended action to mitigate at least one of damage caused by the detected event to the building and injury caused by the detected event to the at least one person associated with the building. The method may include additional, less, or alternate actions, including those discussed elsewhere herein.

For instance, the method may further include generating, based upon the comparison, an alert message that includes the detected event and the recommended action for an owner of the building; and transmitting the alert message to a user computing device associated with the owner of the building. In some embodiments, the recommended action is not implemented until receiving authorization from the owner of the building via their user computing device.

In another aspect, at least one non-transitory computer-readable storage media having computer-executable instructions embodied thereon is provided that are executed by a building analysis ("BA") server communicatively coupled to a plurality of sensors positioned within a building. The plurality of sensors are configured to detect a condition associated with an infrastructure of the building, and the infrastructure is at least one of (i) a fixture associated with the building and (ii) at least one person located within the building. The BA server may include one or more processors in communication with a memory device, the memory device including an optimal profile of the infrastructure, and the optimal profile including characteristics representative of an optimal condition for the infrastructure. The computer-executable instructions cause the one or more processors to: (1) receive, from the plurality of sensors, sensor data related to the infrastructure; (2) compare the received sensor data to the optimal profile to detect an event associated with the infrastructure; (3) determine a recommended action based upon the detected event, wherein the recommended action is at least one of a preventative action or a corrective action; and/or (4) execute the recommended action to mitigate at least one of damage caused by the detected event to the building and injury caused by the detected event to the at least one person associated with the building. The instructions may direct or control additional, less, or alternate functionality, including that discussed elsewhere herein.

For instance, the computer-executable instructions further cause the one or more processors to generate, based upon the comparison, an alert message that includes the detected event and the recommended action for an owner of the building; and transmit the alert message to a user computing device associated with the owner of the building. In some embodiments, the recommended action is not taken until authorization is received via wireless communication from the user computing device associated with the owner of the building.

Machine Learning & Other Matters

The computer-implemented methods discussed herein may include additional, less, or alternate actions, including those discussed elsewhere herein. The methods may be implemented via one or more local or remote processors, transceivers, servers, and/or sensors (such as processors, transceivers, servers, and/or sensors mounted on vehicles or mobile devices, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, a reinforced or reinforcement learning module or program, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics and information, historical estimates, and/or actual repair costs. The machine learning programs may utilize deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing-either individually or in combination. The machine learning programs may also include natural language processing, semantic analysis, automatic reasoning, and/or machine learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In one embodiment, machine learning techniques may be used to extract data about infrastructures and users associated with a building to detect events and correlations between detected events to identify trends.

Based upon these analyses, the processing element may learn how to identify characteristics and patterns that may then be applied to analyzing image data, model data, and/or other data. For example, the processing element may learn, with the user's permission or affirmative consent, to identify the type of building events that occurred based upon collected images of building. The processing element may also learn how to identify building trends that may not be readily apparent based upon collected sensor data.

Additional Considerations

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), SD card, memory device and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer-readable medium. In an example embodiment, the system is executed on a single computer system, without requiring a connection to a server computer. In a further example embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). In a further embodiment, the system is run on an iOS® environment (iOS is a registered trademark of Cisco Systems, Inc. located in San Jose, CA). In yet a further embodiment, the system is run on a Mac OS® environment (Mac OS is a registered trademark of Apple Inc. located in Cupertino, CA). In still yet a further embodiment, the system is run on Android® OS (Android is a registered trademark of Google, Inc. of Mountain View, CA). In another embodiment, the system is run on Linux® OS (Linux is a registered trademark of Linus Torvalds of Boston, MA). The application is flexible and designed to run in various different environments without compromising any major functionality. The following detailed description illustrates embodiments of the disclosure by way of example and not by way of limitation. It is contemplated that the disclosure has general application to providing an on-demand ecosystem in industrial, commercial, and residential applications.

In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A building analysis ("BA") system associated with detecting events of an infrastructure, the infrastructure including a building along with one or more fixtures associated therewith and at least one person located within the building, the BA system comprising:

a plurality of sensors configured to detect a condition of (i) the one or more fixtures and (ii) the at least one person located within the building;

at least one memory; and a building analysis ("BA") computing device communicatively coupled to the plurality of sensors, the BA computing device comprising one or more processors in communication with the at least one memory, wherein the one or more processors are programmed to:

build an infrastructure profile for the infrastructure, the infrastructure profile including i) one or more reference parameters representing normal operating conditions of the one or more fixtures, ii) detected historical conditions of the one or more fixtures using historical sensor data received over a period of time, and iii) detected historical conditions of the at least one person using historical sensor data received over a period of time;

store the infrastructure profile in the at least one memory;

receive updated sensor data;

compare the updated sensor data to the infrastructure profile to determine a new condition associated with the infrastructure;

determine a recommended action for addressing the new condition and a recommended response time to implement the recommended action;

generate, based upon the new condition, an alert message that includes the determined new condition, the recommended action for addressing the new condition, and the recommended response time;

transmit the alert message to a designated user computing device;

determine, over a subsequent period of time, that the recommended action for addressing the new condition has been executed;

generate a historical record of recommended actions including each historical recommended action and whether the respective historical recommended action was executed within the response time;

determine, from the historical record, a rating for the owner representing a number of recommended actions completed within the recommended response time; and transmit, based upon the rating, an offer for at least one of an automobile insurance policy and a life insurance policy.

2. The building analysis system of claim 1, wherein the one or more reference parameters includes one or more optimal operating conditions of the one or more fixtures and one or more threshold levels of the one or more optimal operating conditions of the one or more fixtures.

3. The building analysis system of claim 1, wherein the one or more reference parameters includes one or more optimal conditions of at least one person and one or more threshold levels of the one or more optimal conditions of the at least one person.

4. The building analysis system of claim 1, wherein a fixture of the one or more fixtures is at least one of an electronic device within the building, a utility equipment, and a construction material of the building.

5. The building analysis system of claim 1, wherein the plurality of sensors includes at least one a camera, microphone, air particle sensor, light sensor, and accelerometer.

6. The building analysis system of claim 1, wherein the determined new condition is an environmental new condition within the building, the environmental new condition being a presence of at least one of carbon dioxide, carbon monoxide, smoke, and allergens.

7. The building analysis system of claim 1, wherein the one or more processors are programmed to:

receive, from the plurality of sensors, over a baseline period of time, sample data as to a current condition of a fixture of the one or more fixtures;

generate, based upon the sample data and the reference parameters, a prediction model associated with the fixture; and determine when the fixture needs to be at least one of repaired and replaced by applying the prediction model to the received updated sensor data.

8. The building analysis system of claim 1, wherein the recommended action is at least one of repairing and replacing a fixture of the one or more fixtures.

9. The building analysis system of claim 8, wherein the alert message includes a third-party contact information for performing the recommended action.

10. The building analysis system of claim 1, wherein the alert message notifies an owner of the building as to a potential health hazard due to a current condition of a fixture of the one or more fixtures.

11. The building analysis system of claim 1, wherein the one or more processors are further programmed to:

receive, from the user computing device, a user input accepting or denying the recommended action; and store the user input to the recommended action in the at least one memory.

12. The building analysis system of claim 1, wherein the one or more processors are further programmed to:

determine a priority level of recommended actions;

wherein the lifestyle credit rating is a building owner behavior assessment based upon the priority level of the recommended action.

13. The building analysis system of claim 1, wherein the one or more processors are further programmed to transmit sensor data to a remote-computing device to update an insurance policy associated with an owner of the building.

14. The building analysis system of claim 1, wherein a fixture of the one or more fixtures is a utility equipment, and wherein the one or more processors are further programmed to transmit the updated sensor data to a third-party computing device to detect a utility failure associated with a plurality of buildings.

15. The building analysis system of claim 14 wherein the one or more processors are further programmed to:

transmit, to a user computing device associated with an owner, a request to create a building maintenance savings account to repair the fixture;

receive, from the owner, approval to create the building maintenance savings account and a payment account identifier associated with a payment account of the owner;

link the building maintenance savings account with the payment account; and automatically deposit, from the payment account into the savings account, a designated amount for a predetermined period of time until an amount substantially equal to the estimated cost is within the building maintenance savings account.

16. The building analysis system of claim 1, wherein the one or more processors are further configured to:

compare the updated sensor data to the infrastructure profile, wherein the updated sensor data includes audio data of the at least one person received over a period of time to determine an abnormal noise associated with a health event of the at least one person; and generate, based upon the comparison, a health alert message for an owner of the building.

17. The building analysis system of claim 16, wherein the one or more processors are further configured to differentiate between audio data associated with the one or more fixtures and the at least one person.

18. The building analysis system of claim 16, wherein the health event is at least one of a coughing sound and a sneezing sound.

19. A computer-implemented method for detecting events associated with an infrastructure, the infrastructure including a building with one or more fixtures associated therewith and at least one person periodically located within the building, the method implemented using a computing device that includes at least one processor in communication with at least one memory, the method comprising:

receiving sensor data from a plurality of sensors positioned proximate to the infrastructure, the senor data representative of a condition of (i) the one or more fixtures and (ii) the at least one person periodically located within the building;

building, via the at least one processor, an infrastructure profile for the infrastructure using the senor data, the infrastructure profile including i) one or more reference parameters representing normal operating conditions of the one or more fixtures, ii) detected historical conditions of the one or more fixtures using historical sensor data received over a period of time, and iii) detected historical conditions of the at least one person using historical sensor data received over a period of time;

storing in the at least one memory the infrastructure profile;

receiving updated sensor data from the plurality of sensors;

comparing, via the at least one processor, the updated sensor data to the infrastructure profile to determine a new condition associated with the building;

determining a recommended action for addressing the new condition and a recommended response time to implement the recommended action;

generating based upon the new condition using the at least one processor, an alert message that includes the determined new condition, the recommended action for addressing the new condition, and the recommend response time;

transmitting, via the at least one processor, the alert message to a designated user computing device;

determine, over a subsequent period of time, that the recommended action for addressing the new condition has been executed;

generate a historical record of recommended actions including each historical recommended action and whether the respective historical recommended action was executed within the response time;

determine, from the historical record, a rating for the owner representing a number of recommended actions completed within the recommended response time; and transmit, based upon the rating, an offer for at least one of an automobile insurance policy and a life insurance policy.

* * * * *